US011293042B2

(12) United States Patent
Pedersen et al.

(10) Patent No.: US 11,293,042 B2
(45) Date of Patent: Apr. 5, 2022

(54) OLIGOSACCHARIDE PRODUCTION

(71) Applicant: GLYCOM A/S, Hørsholm (DK)

(72) Inventors: Margit Pedersen, Roskilde (DK);
Manos Papadakis, Copenhagen (DK);
Peter Becker, Virum (DK); Eric Samain, Gieres (FR); Pauline Peltier-Pain, Orleans (FR); Katrine Bych, Valby (DK); Ted Johanson, Virum (DK); Elise Champion, Toulouse (FR); Gyula Dekany, Sinnamon Park (AU)

(73) Assignee: GLYCOM A/S, Hørsholm (DK)

( * ) Notice: Subject to any disclaimer, the term of this patent is extended or adjusted under 35 U.S.C. 154(b) by 0 days.

(21) Appl. No.: 16/927,700

(22) Filed: Jul. 13, 2020

(65) Prior Publication Data

US 2020/0354761 A1 Nov. 12, 2020

Related U.S. Application Data

(63) Continuation-in-part of application No. 15/321,996, filed as application No. PCT/DK2015/050191 on Jun. 29, 2015, now Pat. No. 10,731,193.

(30) Foreign Application Priority Data

Jun. 27, 2014 (DK) .......................... PA 2014 70392

(51) Int. Cl.
C12P 19/00 (2006.01)
C12P 19/12 (2006.01)

(52) U.S. Cl.
CPC ....... C12P 19/12 (2013.01); *C12Y 204/01094* (2013.01)

(58) Field of Classification Search
CPC .................................................. C12P 19/00
See application file for complete search history.

(56) References Cited

U.S. PATENT DOCUMENTS

| | | | |
|---|---|---|---|
| 2008/0145899 A1 | 6/2008 | Johnson et al. | |
| 2009/0082307 A1 | 3/2009 | Samain et al. | |
| 2012/0208181 A1 | 8/2012 | Merighi et al. | |
| 2016/0024543 A1 | 1/2016 | Merighi et al. | |

FOREIGN PATENT DOCUMENTS

| | | |
|---|---|---|
| AU | 200062961 | 4/2001 |
| EP | 1149911 | 10/2001 |
| EP | 1911850 | 4/2008 |
| EP | 2371952 | 10/2011 |
| EP | 2405005 | 1/2012 |
| EP | 2405006 | 1/2012 |
| GB | 2155935 | 10/1985 |
| PL | 2239336 | 10/2010 |
| WO | 2007101862 | 9/2007 |
| WO | 2010051849 | 5/2010 |
| WO | 2010070104 | 6/2010 |
| WO | 2012007481 | 1/2012 |
| WO | 2012078311 | 6/2012 |
| WO | 2012112777 | 8/2012 |
| WO | 2013087884 | 6/2013 |
| WO | 2013182206 | 12/2013 |
| WO | 2014048439 | 4/2014 |
| WO | 2014067696 | 5/2014 |
| WO | 2015150328 A1 | 10/2015 |
| WO | 2019043029 A1 | 3/2019 |
| WO | 2019076941 A1 | 4/2019 |
| WO | 2019123324 A1 | 6/2019 |
| WO | 2020115671 A1 | 6/2020 |

OTHER PUBLICATIONS

Baumgartner, F. et al., "Construction of *Escherichia coli* strains with chromosomally integrated expression cassettes for the synthesis of 2′-fucosyllactose," Microb. Cell Fact., 2013, vol. 12(40), 14 pages.

Bruschi, M. et al., "A transferable sucrose utilization approach for non-sucrose-utilizing *Escherichia coli* strains," Biotechnol. Adv., 2012, vol. 30, 1001-1010.

Chen, X., "Human Milk Oligosaccharides (HMOS): Structure, Function, and Enzyme-Catalyzed Synthesis," Advances in Carbohydrate Chemistry and Biochemistry, 2015, vol. 72, pp. 113-190.

De Bruyn, F. et al., "Development of an in vivo glucosylation platform by coupling production to growth: Production of phenolic glucosides by a glycosyltransferase of Vitis vinifera", Biotechnology and Bioengineering, 2015, vol. 112, pp. 1594-1603.

Drouillard, S. et al., "Large-scale synthesis of H-antigen oligosaccharides by expressing Helicobacter pylori alpha 1,2-fucosyltransferase in metabolically engineered *Escherichia coli* cells," Angew. Chem. Int. Ed., 2006, vol. 45 (11), pp. 1778-1780.

Fort, S. et al., "Biosynthesis of Conjugatable Saccharidic Moieties of GM2 and GM3 Gangliosides by Engineered *E. coli*," Chem. Comm., 2005, vol. 20, pp. 2558-2560.

Gabor, E. et al., "The phosphoenolpyruvate-dependent glucose-phosphotransferase system from *Escherichia coli* K-12 as the center of a network regulating carbohydrate flux in the cell," European Journal of Cell Biology, 2011, vol. 90, pp. 711-720.

Gosset, G., "Improvement of *Escherichia coli* production strains by modification of the phosphoenolpyruvate:sugar phosphotransferase system," Microbial Cell Factories, 2005, vol. 4(14), 11 pages.

Herring, C.D., et al., "Gene replacement without selection: regulated suppression of amber mutations in *Escherichia coli*," Gene, 2003, vol. 331, pp. 153-163.

Jahreis, K. et al., "Adaptation of Sucrose Metabolism in the *Escherichia coli* Wild-Type Strain EC3132," Journal of Bacteriology, 2002, vol. 184(19), pp. 5307-5316.

Khamduang, M. et al., "Production of L-phenylalanine from glycerol by a recombinant *Escherichia coli*," J. Ind. Microbiol. Biotechnol., 2009, vol. 36, pp. 1267-1274.

(Continued)

*Primary Examiner* — Tekchand Saidha
(74) *Attorney, Agent, or Firm* — Neal, Gerber & Eisenberg LLP

(57) ABSTRACT

The invention relates to a genetically modified microorganism for making a oligosaccharide, preferably of 3-8 monosaccharide units, more preferably of 3-5 monosaccharide units, particularly a HMO, which comprises one or more genes encoding a sucrose utilization system, so the microorganism can use sucrose as a carbon and energy source.

13 Claims, 1 Drawing Sheet

(56) References Cited

OTHER PUBLICATIONS

Kim, J. R. et al., "Construction of homologous and heterologous synthetic sucrose utilizing modules and their application for carotenoid production in recombinant *Escherichia coli*," Biores. Technol., 2013, vol. 130, pp. 288-295.

Lee, W. et al., "Whole cell biosynthesis of a functional oligosaccharide, 2'-fucosyllactose, using engineered *Escherichia coli*," Microb. Cell Fact., 2012, vol. 11(48), 10 pages.

Olson, M. M. et al., "Production of tyrosine from sucrose or glucose achieved by rapid genetic changes to phenylalanine-producing *Escherichia coli* strains," Appl. Microbiol. Biotechnol., 2007, vol. 74, pp. 1031-1040.

PLOS Collections. (Oct. 26, 2017). Negative Results: A Crucial Piece of the Scientific Puzzle [Blog post]. Retrieved from https://blogs.plos.org/everyone/2017/10/26/negative-results-a-crucial-piece-of-the-scientific-puzzle/.

Postma, P. W. et al., "Phosphoenolpyruvate:Carbohydrate Phosphotransferase Systems of Bacteria," Microbiological Reviews, 1993, vol. 57(3), pp. 543-594.

Priem, B. et al., "A new fermentation process allows large-scale production of human milk oligosaccharides by metabolically engineered bacteria", Glycobiology, 2002, vol. 12(4), pp. 235-240.

Reid, S. J. et al., "Sucrose utilisation in bacteria: genetic organisation and regulation," Appl. Microbiol. Biotechnol., 2005, vol. 67, pp. 312-321.

Ruffing, A. et al., "Metabolic engineering of *Agrobacterium* sp. for UDP-galactose regeneration and oligosaccharide synthesis", Metabolic Engineering, 2006, vol. 8, pp. 465-473.

Ruffing, A. et al., "Metabolic engineering of microbes for oligosaccharide and polysaccharide synthesis", Microbial Cell Factories, 2006, vol. 5(25), 9 pages.

Sabri, S. et al., "Molecular Control of Sucrose Utilization in *Escherichia coli* W, an Efficient Sucrase-Utilizing Strain," Appl. Environ. Microbiol, 2013, vol. 79(2), pp. 478-487.

Schmid, K. et al., "Plasmid-Mediated Sucrose Metabolism in *Escherichia coli* K12: Mapping of the scr Gene of pUR400", Molecular Microbiology, 1988, vol. 2(1), pp. 1-8.

Titgemeyer, F. et al., "Molecular analysis of the scrA and scrB genes from Klebsiella pneumoniae and plasmid pUR400, which encode the sucrose transport protein Enzyme User of the phosphotransferase system and a sucrose-6-phosphate invertase," Mol. Gen. Genet., 1996, vol. 250, pp. 197-206.

Varki A, Cummings RD, Esko JD, et al., editors. Essentials of Glycobiology. 2nd edition. Cold Spring Harbor (NY): Cold Spring Harbor Laboratory Press; 2009 16 pages.

Wang, J. et al., "Modeling of inducer exclusion and catabolite repression based on a PTS-dependent sucrose and non-PTS-dependent glycerol transport systems in *Escherichia coli* K-12 and its experimental verification," Journal of Biotechnology, 2001, vol. 92, pp. 133-158.

Warming, S., et al., "Simple and highly efficient BAC recombineering using galK selection," Nucleic Acids Research, 2005, vol. 33(4), pp. 1-12.

Urashima, T. et al. (2011) Nutrition and Diet Research Progress: Milk Oligosaccharides. New York: Nova Science Publishers, Inc. 92 pages.

Bruschi et al., "A transferable sucrose utilization approach for non-sucrose-utilizing *Escherichia coli* strains," Biotechnol. Adv., 2012, vol. 30, 1001-1010.

Khamduang et al., "Production of L-phenylalanine from glycerol by a recombinant *Escherichia coli*," J. Ind. Microbiol. Biotechnol., 2009, vol. 36, pp. 1267-1274.

Mohamed, E.T., et al., "Generation of an *E. coli* platform strain for improved sucrose utilization using adaptive laboratory evolution," Microbial Cell Factories, 2019, vol. 18, pp. 1-14.

Response to Non-Final Office Action filed Sep. 23, 2019 in U.S. Appl. No. 15/321,996, now U.S. Pat. No. 10,731,193, 21 pages.

Response to Final Office Action filed Feb. 15, 2019 in U.S. Appl. No. 15/321,996, now U.S. Pat. No. 10,731,193, 18 pages.

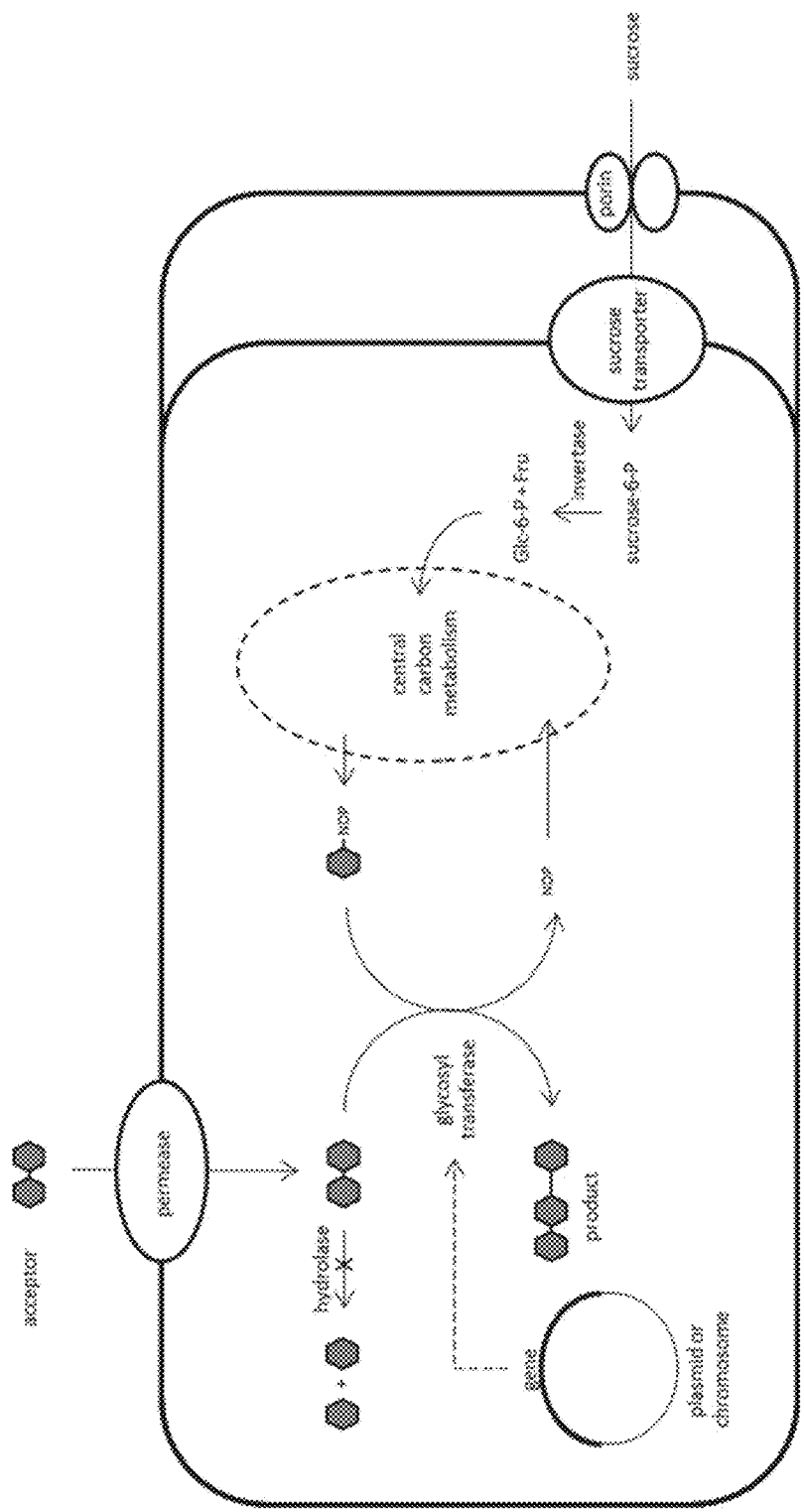

OLIGOSACCHARIDE PRODUCTION

CROSS-REFERENCE TO RELATED APPLICATIONS

This application is a continuation-in-part of U.S. application Ser. No. 15/321,996, filed Dec. 23, 2016, which is a national stage filing in accordance with 35 U.S.C. § 371 of PCT/DK2015/050191, filed Jun. 29, 2015, which claims the benefit of the priority of Denmark Patent Application No. PA 2014 70392, filed Jun. 27, 2014, the contents of each are incorporated herein by reference.

FIELD OF THE INVENTION

The present invention relates to the field of biotechnology, notably to a microbial production of oligosaccharides, particularly of human milk oligosaccharides (HMOs), using a genetically modified microorganism, particularly *E. coli*, using sucrose as its exclusive carbon source.

BACKGROUND OF THE INVENTION

The fermentative syntheses of foreign or exogenous oligosaccharides using recombinant microorganisms have recently become of great commercial and industrial interest. In such syntheses, oligosaccharides of interest would be synthesized by enzymatic glycosylation of sugar acceptors mediated by one or more heterologous glycosyl transferases of the microorganisms, and the one or more activated sugar nucleotides necessary for glycosylation would be produced by the same microorganism through overexpressing one or more genes encoding endogenous activated sugar nucleotide producing enzymes. The metabolic pathways of such syntheses require a carbon source which is mainly a simple carbon building block, typically glycerol or glucose (see e.g. WO 01/04341, Priem et al. *Glycobiology* 12, 235 (2002), Fort et al. *Chem. Comm.* 2558 (2005), Drouillard et al. *Angew. Chem. Int. Ed.* 45, 1778 (2006), WO 2010/070104, WO 2012/112777, WO 2013/182206, WO 2014/048439). In some syntheses, lactose can be the carbon source if it also serves as an acceptor (Lee et al. *Microb. Cell Fact.* 11:48 (2012)). As the microorganisms have been genetically manipulated, antibiotic-resistance selection marker genes have been utilized to separate the transformed microorganisms from the non-transformed ones in the inoculum and the fermentation broth. However, the use of antibiotics has been avoided by integrating the genes coding for enzymes involved in the de novo biosynthesis of the donor sugar in the chromosome of the microorganisms (Baumgartner et al. *Microb. Cell Fact.* 12:40 (2013)).

Around 50% of wild-type *E. coli* are able to utilize sucrose as a carbon and energy source, but most of them are pathogenic. The *E. coli* strains used mainly in industry to synthesize chemical materials cannot live and grow on sucrose (Bruschi et al. *Biotechnol. Adv.* 30, 1001 (2012)). However, in some cases, sucrose can be a cheaper carbon and energy source. For this reason, attempts have been made to create suck strains of *E. coli* that can live and grow on sucrose (e.g. GB 2155935 A, Sabri et al. *Appl. Environ. Microbiol* 79, 478 (2013)) and produce industrially profitable products by them such as amino acids, biofuel, carotenoids etc. (e.g. EP-A-1149911, EP-A-2239336, EP-A-2371952, EP-A-2405006, WO 2010/051849, WO 2012/078311, Kim et al. *Biores. Technol.* 130, 288 (2013)). However, these suck transformants have generally been less productive than suc$^-$ strains (Khamduang et al. *J. Ind. Microbiol.* Biotechnol. 36, 1267 (2009)).

WO 2012/007481 describes *E. coli* transformants that express either a sucrose phosphorylase or a sucrose invertase in combination with a fructokinase. Thereby, the microorganism is able to produce 2'-fucosyllactose, utilizing sucrose as its main carbon source. Furthermore, WO 2014/067696, WO 2015/150328, WO 2019/043029 and WO 2019/076941 describe *E. coli* transformants comprising a csc-gene cluster that enables them to grow on sucrose and produces fucose, 2'-FL, sialyllactose and sialic acid, respectively.

There has been, however, a continuing need for alternative processes for making oligosaccharides, particularly HMOs, using transformed microorganisms that are able to utilize more effectively sucrose as a carbon and energy source.

SUMMARY OF THE INVENTION

A first aspect of the invention relates to a process for making an oligosaccharide, preferably of 3-8 monosaccharide units, more preferably of 3-5 monosaccharide units, particularly a HMO, by glycosylating a carbohydrate acceptor which is not sucrose, preferably lactose, comprising the steps of:

a) providing a cell, preferably an *E. coli* cell, that can internalize said acceptor into said cell and comprises
   a recombinant gene encoding a glycosyl transferase which is able to transfer a glycosyl residue of an activated sugar nucleotide to said acceptor, internalized in said cell, or to an intermediate in the biosynthetic pathway to said oligosaccharide from said acceptor and
   a biosynthetic pathway to make said activated sugar nucleotide in said cell, b) culturing said cell in the presence of said acceptor and sucrose, and c) separating said oligosaccharide from said cell, from the culture medium or from both, said process being characterized in that said cell also comprises one or more genes encoding a sucrose utilization system, preferably encoding a heterologous sucrose utilization system, more preferably encoding a heterologous PTS-dependent sucrose utilization transport system, still more preferably scr genes, so that said cell can use sucrose as a carbon source, preferably the main carbon source, more preferably the sole carbon source, for making said activated sugar nucleotide and as an energy source, preferably the main energy source, more preferably the sole energy source, for making said oligosaccharide.

A second aspect of the invention relates to a cell, preferably an *E. coli* cell, that can internalize a carbohydrate acceptor, which is not sucrose, preferably lactose, into said cell and that comprises:
   a recombinant gene encoding a glycosyl transferase which is able to transfer a glycosyl residue of an activated sugar nucleotide to said acceptor, internalized in said cell, or to an intermediate in the biosynthetic pathway to said oligosaccharide from said acceptor
   a biosynthetic pathway to make said activated sugar nucleotide in said cell, and
   one or more genes encoding a sucrose utilization system, preferably a heterologous sucrose utilization system, more preferably scr genes, so that said cell can use sucrose as a carbon source, preferably the main carbon source, more preferably the sole carbon source.

BRIEF DESCRIPTION OF THE FIGURE

The FIGURE is intended to illustrate the invention further. It is not intended to limit the subject matter of the invention thereto.

The engineered microorganism is a fully metabolically active cell in which the growth and the oligosaccharide synthesis may proceed simultaneously. The cell comprises a heterologous PTS-dependent sucrose utilization transport system containing a sucrose specific porin (facilitates the sucrose diffusion through the outer membrane), a sucrose transport protein (provides intracellular sucrose-6-phosphate from extracellular sucrose) and a sucrose-6-phosphate hydrolase (provides glucose-6-phosphate and fructose). The oxidation of glucose-6-phosphate and fructose provides biological energy source by the organism's own metabolic system. Also, glucose-6-phosphate and fructose serve as carbon source for producing sugar nucleotides in the cell's natural biosynthetic pathway or in any heterologous pathway expressed in the cell. The so-produced sugar nucleotides are donors for glycosylating carbohydrate acceptors (e.g. lactose), internalized through a specific permease by the cell, and thereby manufacturing oligosaccharides of interest. The glycosylation is mediated by one or more glycosyl transferases which are directly produced by expressing heterologous genes from plasmid or the chromosome. The organism lacks any enzyme degrading either the acceptor or the oligosaccharide product in the cell.

DETAILED DESCRIPTION OF THE INVENTION

It has been surprisingly discovered that an exogenous mono- or disaccharide acceptor, preferably lactose, can be internalized in a suitable genetically transformed microorganism, particularly E. coli, by a transport mechanism of the microorganism, so that this carbohydrate acceptor can be glycosylated in the microorganism using sucrose as its carbon and energy source, and that an exogenous oligosaccharide can be produced and separated in good yield. Thereby, an efficient, cheap and easily up-scalable process for producing oligosaccharides can be obtained. In order to make the process successful, a special oligosaccharide-producing microorganism is needed that can live on sucrose, utilize sucrose for the metabolic syntheses of the necessary nucleotide sugar donors for glycosylation, can internalize simple carbohydrate acceptors and perform glycosylation reactions on them for synthesizing more complex oligosaccharides.

The invention therefore, in a first aspect, involves a process of making an oligosaccharide by:
a) providing a cell of a microorganism, preferably an E. coli cell, that can internalize sucrose and a carbohydrate acceptor, preferably lactose, into said cell and that comprises:
   a recombinant gene encoding a glycosyl transferase which can transfer a glycosyl residue of an activated sugar nucleotide to the acceptor within the cell or to an intermediate in the biosynthetic pathway to said oligosaccharide from said acceptor, and
   a biosynthetic pathway for making the activated sugar nucleotide from sucrose,
b) culturing the cell in an aqueous culture medium in the presence of the acceptor and sucrose, and
c) separating the oligosaccharide product from the cell from the culture medium or from both.

The process features the cell being transformed with one or more foreign genes encoding a sucrose utilization system that allows the cell to use sucrose as a carbon source, preferably the main carbon source, more preferably the sole carbon source, for the biosynthesis of the activated sugar nucleotide by the cell. The sucrose utilization system, with which the cell is transformed, also preferably allows the cell to use sucrose as an energy source, preferably the main energy source, more preferably the sole energy source, for the biosynthesis of the oligosaccharide.

In accordance with this invention, the term "carbohydrate acceptor" or "acceptor" preferably means a mono- or disaccharide other than sucrose and its glycosides. A monosaccharide acceptor or a monosaccharide part of a disaccharide acceptor can comprise any 5-6 carbon atom sugar moiety that is an aldose (e.g. D-glucose, D-galactose, D-mannose, D-ribose, D-arabinose, L-arabinose, D-xylose, etc.), ketose (e.g. D-fructose, D-sorbose, D-tagatose, etc.), deoxysugar (e.g. L-rhamnose, L-fucose, etc.) or deoxy-aminosugar (e.g. N-acetylglucosamine, N-acetylmannosamine, N-acetylgalactosamine, etc.). In a glycoside-type carbohydrate acceptor the sugar moiety is attached to a non-sugar residue (aglycon) by either a covalent bond, which is a direct linkage between the glycosidic carbon atom of the sugar residue and any atom of the non-sugar moiety, or by a linker, which consists of one, two, three or four atoms such as —O—, —C—, —NH—, —N(OH)—, —S—, —C(=O)—, —C(=S)—, —C(=NH)—, —C(=N—OH)—, —C(=O)—O—, —O—C(=O)—, —C(=O)—S—, —S—C(=O)—, —C(=S)—O—, —O—C(=S)—, —C(=S)—S—, —S—C(=S)—, —C(=O)—NH—, —NH—C(=O)—, —C(=NH)—O—, —O—C(=NH)—, —C(=S)—NH—, —NH—C(=S)—, —C(=NH)—S— and —S—C(=NH). Thus, the C-1 (in case of aldoses) or C-2 (in the case of ketoses) anomeric carbon atom at the reducing end of the mono- or disaccharide residue is linked to the non-sugar moiety by a covalent bond or a linker forming a O-, N-, S- or C-glycoside. Preferably, the aglycon of these glycosidic derivatives, with or without a linker, is one of the following groups:

a) —$OR_A$, wherein $R_A$ is a linear or branched hydrocarbon chain having, when saturated, 1-24, preferably 1-6 carbon atoms (such as methyl, ethyl, n-propyl, i-propyl, n-butyl, i-butyl, s-butyl, t-butyl, n-hexyl, etc.) or, when unsaturated, 2-24, preferably 2-6 carbon atoms (such as vinyl, allyl, propargyl, etc.), or $R_A$ means an aryl moiety (a homoaromatic group such as phenyl or naphthyl), or $R_A$ means a group removable by hydrogenolysis, that is a group whose bond attached to the oxygen can be cleaved by addition of hydrogen in the presence of catalytic amounts of palladium, Raney nickel or another appropriate metal catalyst known for use in hydrogenolysis, resulting in the regeneration of an OH group; such protecting groups are well known to the skilled man and are discussed in *Protective Groups in Organic Synthesis*, PGM Wuts and TW Greene, John Wiley & Sons 2007. Suitable groups include benzyl, diphenylmethyl (benzhydryl), 1-naphthylmethyl, 2-naphthylmethyl or triphenylmethyl (trityl) groups. Any of the above mentioned $R_A$ groups can be optionally substituted by one or more groups selected from: alkyl (only for aryl and group removable by hydrogenolysis), hydroxy, alkoxy, carboxy, oxo, alkoxycarbonyl, alkylcarbonyl, formyl, aryl, aryloxy-carbonyl, aryloxy, arylamino, arylcarbonyl, amino, mono and dialkylamino, carbamoyl, mono- and dialkyl-amino-carbonyl, alkyl-carbonylamino, cyano, alkanoyloxy, nitro, alkylthio and halogen; in case of a group removable by hydrogenolysis, such substitution, if present, is preferably on the aromatic ring(s);

b) —X—$R_B$, wherein X is N or S, and $R_B$ means linear or branched hydrocarbon chain having, when saturated, 1-24, preferably 1-6 carbon atoms (such as methyl, ethyl, n-propyl, i-propyl, n-butyl, i-butyl, s-butyl, t-butyl, n-hexyl, etc.) or, when unsaturated, 2-24, preferably 2-6 carbon atoms (such as vinyl, allyl, propargyl, etc.), or $R_B$ means an aryl moiety (a homoaromatic group such as phenyl or naphthyl), or $R_B$ means a benzyl group. Any of the above mentioned $R_B$ groups can be optionally substituted by one or more groups selected from: alkyl (only for aryl and benzyl), hydroxy, alkoxy, carboxy, oxo, alkoxycarbonyl, alkylcarbonyl, formyl, aryl, aryloxy-carbonyl, aryloxy, arylamino, arylcarbonyl, amino, mono and dialkylamino, carbamoyl, mono- and dialkyl-amino-carbonyl, alkyl-carbonylamino, cyano, alkanoyloxy, nitro, alkylthio and halogen;

c) a group that links the anomeric carbon atom and the adjacent carbon atom to each other by a —NH—C(=O)—O-bridge, thus forming a fused 5-membered ring as depicted below in case of an aldose:

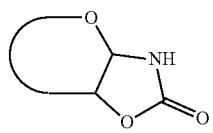

d) azide;

e) —NH—C(R″)=C(R′)$_2$, wherein each R′ independently is an electron withdrawing group selected from —CN, —COOH, —COO-alkyl, —CO-alkyl, —CONH$_2$, —CONH-alkyl and —CON(alkyl)$_2$, or wherein the two R′-groups are linked together and form —CO—(CH$_2$)$_{2-4}$—CO— and thus form with the carbon atom, to which they are attached, a 5-7 membered cycloalkane-1,3-dione, in which dione any of the methylene groups is optionally substituted with 1 or 2 alkyl groups, and wherein R″ is H or alkyl;

f) a residue of an amino acid, which can be any natural or non-natural amino acid, that is an alkanoic acid derivative having at least one amino group as a substituent. Preferably, the amino acid is selected from the group consisting of: α-amino acids and β-amino acids such as Ala, Arg, Asn, Asp, Cys, Glu, Gln, Gly, His, Ile, Leu, Lys, Met, Phe, Pro, Ser, Thr, Trp, Tyr, Val, hydroxyproline, α-methylserine, β-alanine, etc. These amino acids can be either directly or via a linker as defined above (e.g. for urea-linked glycopeptides see WO 2009/040363) bound to the carbohydrate at its C-1 (in case of aldoses) or C-2 (in the case of ketoses) anomeric carbon atom thus forming O-, N-, S- or C-glycosides. 0-Glycosides (0-glycans) can be formed involving OH-containing amino acids such as serine, threonine, hydroxyproline, etc., N-glycosides (N-glycans) can be made using the α-, β-, etc. amino group of any amino acid or the additional amino group of the side chain of e.g. lysine, asparagine or glutamine, S-glycosides can be made using cysteine, while C-glycosides (C-glycans) contain a C—C bond coupling a C-atom of the amino acid to the anomeric carbon atom of the non-reducing end of the oligosaccharide part;

g) a polyethylene glycol residue. Polyethylene glycol (PEG) is a water soluble polyether of molecular formula $C_{2n}H_{4n+2}O_{n+1}$, having oxyethylene (—CH$_2$—O—CH$_2$— or CH$_2$—CH$_2$—O—) repeating units and wherein n is 2 to 100, preferably 2 to 50, particularly 2 to 25, more particularly 2 to 10. Lower molecular weight PEGs are available in a purified form and are referred to as a "monodisperse PEG", and are also available as mixtures of PEGs and are referred to as a "polydisperse PEG". With regard to their geometry, PEGs can be in a linear, branched, star or comb configuration. Linear PEGs are preferably lower molecular weight PEGs (i.e., n is 2 to 10, preferably 3 to 6). Branched PEGs preferably have 3 to 10 linear, preferably lower molecular weight, PEG chains emanating from a central core group. Star PEGs preferably have 10 to 100 linear or branched, preferably lower molecular weight, PEG chains emanating from a central core group. Comb PEGs have multiple linear, branched and/or star, preferably lower molecular weight, PEG chains bonded to a polymer backbone. Terminal primary hydroxy group of PEGs can be bonded by an ether bond with an alkyl group, preferably methyl. In addition, their terminal hydroxy group can be replaced by amino, alkyl amino, dialkyl amino, acylamino, thiol or alkyl thio groups or their terminal hydroxymethyl group can be oxidized to a carboxyl, which can be esterified or be present in amide form with ammonia or a primary or secondary amine. The attachment is a glycosidic-like bond;

h) a polyvinyl alcohol residue. Polyvinyl alcohol (PVA) is a water-soluble polymer of molecular formula $(C_2H_4O)_x$ having —CH$_2$—CH(OH)— monomer units, wherein x is any desired integer. When attached to carbohydrate, any of the OH-groups can be glycosylated;

i) an α,β-unsaturated amido group of formula A

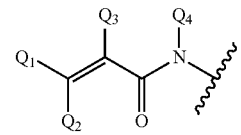

wherein $Q_1$, $Q_2$, $Q_3$ and $Q_4$ are, independently, H and $C_1$-$C_6$-alkyl, which alkyl optionally can be substituted with halogen, OH, nitro or phenyl groups. The residue of formula A, via its N atom, is linked to the sugar by a covalent bond, preferably to the anomeric carbon atom of the carbohydrate in the form of an N-glycoside; or j) an α,β-unsaturated carbonyl group of formula B

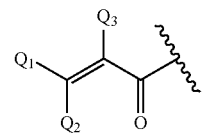

wherein $Q_1$, $Q_2$ and $Q_3$ are as defined at residue of formula A.

Preferably, the carbohydrate acceptor is a galactosyl disaccharide, particularly lactose.

Also in accordance with this invention, the term "oligosaccharide product" or "oligosaccharide" preferably means a glycosylated derivative of a carbohydrate acceptor disclosed above wherein a glycosyl residue is attached to the carbohydrate moiety of the carbohydrate acceptor by inter-glycosidic linkage. Preferably, an oligosaccharide product is of 3-8 monosaccharide units, particularly of 3-5 monosaccharide units, more particularly of 4 monosaccharide units or of 3 monosaccharide units. The oligosaccharide product of this invention is a recombinant product, i.e. it is made by a genetically transformed microorganism and is foreign or heterologous to the microorganism.

The genetically modified microorganism or cell used in the process of some embodiments of this invention can be selected from the group consisting of bacteria and yeasts, preferably a bacterium. Bacteria are preferably selected from the group of: *Escherichia coli*, *Bacillus* spp. (e.g. *Bacillus subtilis*), *Campylobacter pylori*, *Helicobacter pylori*, *Agrobacterium tumefaciens*, *Staphylococcus aureus*, *Thermophilus aquaticus*, *Azorhizobium caulinodans*, *Rhizobium leguminosarum*, *Neisseria gonorrhoeae*, *Neisseria meningitis*, *Lactobacillus* spp., *Lactococcus* spp., *Enterococcus* spp., *Bifidobacterium* spp., *Sporolactobacillus* spp., *Micromomospora* spp., *Micrococcus* spp., *Rhodococcus* spp., *Pseudomonas*, among which *E. coli* is preferred.

Further in accordance with some embodiments of this invention, the microorganism or cell, preferably an *E. coli* cell, is genetically modified so that there is at least one alteration in its DNA sequence. The alteration can result in a change in the original characteristics of the wild type cell, e.g. the modified cell is able to perform additional chemical transformation due to the introduced new genetic material that encodes the expression of an enzymes not being in the wild type cell, or is not able to carry out transformation like degradation due to removal or deactivation of gene/genes. In this regard, a genetically modified cell contains at least one artificial alteration in its genome compared to its naturally occurring (wild type) variant. By the alteration, either a nucleic acid construct is added to the cell by way of integration into the genome or by addition via plasmid, or a nucleic acid sequence is deleted from or changed in the genome of the cell. Whatever is the case, the so-transformed cell has a genotype that is different from that before the alteration and, therefore, the modified cell shows modified feature(s). Preferably, the genetically modified cell can perform at least one additional or altered biochemical reaction, when cultured or fermented, due to the introduction of a heterologous nucleic acid sequence or the modification of a native nucleic acid sequence that encodes an enzyme that is not expressed in the wild type cell, or the genetically modified cell cannot perform a biochemical reaction due to the deletion, addition or modification of a nucleic acid sequence that encodes an enzyme found in the wild type cell. The genetically modified cell can be constructed by well-known, conventional genetic engineering techniques (e.g. Green and Sambrook: *Molecular Cloning: A laboratory Manual*, 4$^{th}$ ed., Cold Spring Harbor Laboratory Press (2012); *Current protocols in molecular biology* (Ausubel et al. eds.), John Wiley and Sons (2010)). The terms "host cell", "recombinant microorganism or cell" or "genetically modified microorganism or cell" are used interchangeably to designate such constructs.

The term "nucleic acid sequence encoding a polypeptide having a glycosyl transferase activity" or "nucleic acid sequence encoding glycosyl transferase" means a gene, a functional fragment thereof or a codon-optimized version thereof that express a polypeptide having a glycosyl transferase activity.

The term "gene" in the present context relates to a coding nucleic acid sequence.

The term "promoter" means a nucleic acid sequence involved in the binding of RNA polymerase to initiate transcription of an operably linked gene, wherein the gene includes a coding DNA sequence and other (non-coding) sequences, e.g. the 5'-untranslated region (5'-UTR) located upstream of the coding sequence, which comprises a ribosomal binding site. A promoter in some embodiments of this invention is an isolated DNA sequence, i.e. not an integrated DNA fragment of the genomic DNA. The nucleotide sequence of a promoter corresponds to, or have at least 80% identity, preferably 90-99.9% identity with the nucleotide sequence of a fragment of bacterial genomic DNA that is regarded as promoter region of a gene, e.g. a promoter region of a glp operon or lac operon of *E. coli*. By "operon" is meant a functioning unit of genomic DNA containing a cluster of genes under the control of a single promoter. By "glp operon" is meant a cluster of genes involved in the respiratory metabolism of glycerol of bacteria. Preferably, a glp operon promoter sequence comprised in a DNA construct corresponds to or has at least 80% identity, preferably 90-99.9% identity with the nucleotide sequence of a fragment of the genomic DNA regarded as a promoter region of the corresponding glp operon of *E. coli*; in particular, the isolated sequence of a promoter of a glp operon of some embodiments of the invention corresponds to, or has said percent of identity with a fragment of the genomic sequence upstream the sequence having GenBank ID: EG10396 (glpFKX), EG10391 (glpABC), EG10394 (glpD), EG10401 (glpTQ). The *E. coli* genome is referred herein to the complete genomic DNA sequence of *E coli* K-12 MG1655 (GenBank ID:U00096.3).

In some embodiments, a promoter of the glp operon is operably linked to the heterologous glycosyl transferase genes and/or the heterologous scr genes. Preferably, those genes are expressed under a glpF promoter (WO 2019/123324, the content of which is incorporated herein by reference). The process of some embodiments of this invention also involves transporting the exogenous carbohydrate acceptor, preferably lactose, into the genetically modified microorganism for glycosylation to produce a foreign oligosaccharide of interest, preferably without adversely affecting the basic functions of the cell or destroying its integrity. In one embodiment, the transport takes place via a passive mechanism, during which the exogenous acceptor diffuses passively across the plasma membrane of the cell. Diffusion of the acceptor into the microorganism is a function of the concentration differences between the fermentation broth and the extra- and intracellular space of the cell with respect to the acceptor, whereby the acceptor passes from the place of higher concentration to the place of lower concentration. In another embodiment, the acceptor is internalized with the aid of an active transport. In such a case, the genetically modified microorganism contains transporter proteins, called permeases, which act as enzymes and with which the microorganism is able to admit exogenous substances and to concentrate them in the cytoplasm. Specifically, lactose permease (LacY) acts specifically on galactose, simple galactosyl disaccharides such as lactose and their glycosides. The specificity towards the sugar moiety of the exogenous carbohydrate acceptor to be internalized can be altered by mutation of the microorganism by means of conventional recombinant DNA manipulation techniques. In a preferred embodiment, the internalization of exogenous lactose or its derivative takes place via an active transport mechanism mediated by a lactose permease. The genetically modified microorganism preferably lacks any enzyme activity (such as LacZ) that would degrade the acceptor. Likewise, the microorganism is not able to hydrolyze or degrade the oligosaccharide product or any oligosaccharide intermediate in the biosynthetic pathway to the oligosaccharide product.

Moreover, the genetically modified cell used in the process of the invention comprises one or more endogenous or recombinant genes encoding one or more glycosyl transferase enzymes that are able to transfer the glycosyl residue of an activated sugar nucleotide to the internalized acceptor. The gene or an equivalent DNA sequence thereof, if it is recombinant, can be introduced into the cell by conventional techniques, e.g. using an expression vector or by chromosomal integration. The origin of the heterologous nucleic acid sequence can be any animal (including human) or plant, eukaryotic cells such as those from *Saccharomyces cerevisiae, Saccharomyces pombe, Candida albicans* or from algae, prokaryotic cells such as those originated from *E. coli, Bacteroides fragilis, Photobacterium sp., Bacillus subtilis, Campylobacter pylori, Helicobacter pylori, Agrobacterium tumefaciens, Staphylococcus aureus, Thermophilus aquaticus, Azorhizobium caulinodans, Rhizobium leguminosarum, Rhizobium meliloti, Neisseria gonorrhoeae* and *Neisseria meningitidis*, or virus. The glycosyl transferase enzyme/enzymes encoded and expressed by the gene(s) or equivalent DNA sequence(s) are preferably glucosyl transferases, galactosyl transferases, N-acetylglucosaminyl transferases, N-acetylgalactosaminyl transferases, glucuronosyl transferases, xylosyl transferases, mannosyl transferases, fucosyl transferases, sialyl transferases and the like. In a preferred embodiment, the glycosyl transferases are selected from the group consisting of β-1,3-N-acetylglucosaminyl-transferase, β-1,6-N-acetylglucosaminyl-transferase, β-1,3-galactosyl-transferase, β-1,4-galactosyl-transferase, β-1,3-N-acetylgalactosaminyl-transferase, β-1,3-glucuronosyl-transferase, α-2,3-sialyl-transferase, α-2,6-sialyl-transferase, α-2,8-sialyl-transferase, α-1,2-fucosyl-transferase, α-1,3-fucosyl-transferase and α-1,4-fucosyl-transferase. More preferably, the glycosyl transferases are selected from β-1,3-N-acetylglucosaminyl transferase, β-1,6-N-acetylglucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and α-1,4 fucosyl transferase, that is from those involved in the construction of HMO core structures as well as fucosylated and/or sialylated HMOs and its glycosidic derivatives, wherein the aglycon is a moiety defined above at the group of carbohydrate acceptors. The genes encoding the above-mentioned transferases have been described in the literature.

The genetically modified microorganism or cell used in the process of the invention is capable of producing an oligosaccharide from the internalized precursor/acceptor which is preferably lactose. Said cell possesses enzymatic activity that is necessary for synthesizing an oligosaccharide, from an internalized mono- or disaccharide via consecutive glycosylation steps, wherein the internalized acceptor, e.g. lactose, is glycosylated, in a first glycosylation step, to a trisaccharide, then that trisaccharide is glycosylated, in a second glycosylating step, to a tetrasaccharide, and so forth. The glycosylation steps are mediated by respective glycosyl transferases. In this regard, the phrase "a glycosyl transferase which is able to transfer a glycosyl residue of an activated sugar nucleotide to an intermediate in the biosynthetic pathway to said oligosaccharide from said acceptor" or "a glycosyl transferase which can transfer a glycosyl residue of an activated sugar nucleotide to an intermediate in the biosynthetic pathway to said oligosaccharide from said acceptor" refers to the second, third etc. glycosylation step. For example, if lacto-N-tetraose is made from lactose, a first glycosyl transferase (a β-1,3-N-acetyl-glucosaminyl transferase transfers GlcNAc of UDP-GlcNAc to the internalized lactose to form lacto-N-triose II, then a second glycosyl transferase (a β-1,3-galactosyl transferase) transfers Gal of UDP-Gal to the previously formed lacto-N-triose II. In this regard, lacto-N-triose is considered to be an intermediate in the biosynthetic pathway to LNT from lactose.

In the glycosyl transferase mediated glycosylation processes of this invention, activated sugar nucleotides serve as donors, and the glycosyl transferase in question transfers a monosaccharide of an appropriate donor molecule to the acceptor molecule. Each activated sugar nucleotide generally comprises a phosphorylated glycosyl residue attached to a nucleoside, and the specific glycosyl transferase enzyme accepts only the specific sugar nucleotide. Thus, preferably the following activated sugar nucleotides are involved in the glycosyl transfer: UDP-Glc, UDP-Gal, UDP-GlcNAc, UDP-GalNAc, UDP-glucuronic acid, UDP-Xyl, GDP-Man, GDP-Fuc and CMP-sialic acid, particularly those selected from the group consisting of UDP-Gal, UDP-GlcNAc, GDP-Fuc and CMP-sialic acid.

The genetically modified microorganism used in the process of this invention possesses a biosynthetic pathway to the above mentioned activated sugar nucleotides, that is, it has one or more sets of genes encoding one or more enzymes responsible for the synthesis of one or more activated glycosyl nucleotides, ready for glycosylation in glycosyl transferase mediated reaction in the cell, when cultured. The sets of genes are either naturally present in the cell or introduced into the cell by means of recombinant DNA manipulation techniques. The production of the activated glycosyl nucleotides by the cell takes place under the action of enzymes involved in the biosynthetic pathway of that respective sugar nucleotide stepwise reaction sequence starting from a carbon source (for a review for monosaccharide metabolism see e.g. H. H. Freeze and A. D. Elbein: *Chapter 4: Glycosylation precursors*, in: Essentials of Glycobiology, $2^{nd}$ edition (Eds. A. Varki et al.), Cold Spring Harbour Laboratory Press (2009)).

It should be emphasized, that the production of the activated sugar nucleotides by the genetically modified microorganism via its own biosynthetic pathway is advantageous compared to in vitro versions of transfer glycosylation, as it avoids using the very expensive sugar nucleotide type donors added exogenously, hence the donors are formed by the cell in situ and the phosphatidyl nucleoside leaving groups are recycled in the cell.

In addition, the microorganism used in the process of the invention comprises genes encoding a sucrose utilization system, that is the cell has a capability to catabolically utilize sucrose as a carbon source, as well as an energy source. The system that enables the cell to utilize sucrose can be one normally found in the gene pool of that cell but preferably is a heterologous system (i.e. derived from a different organism and transferred to the host cell by conventional recombinant DNA manipulation techniques). Typically, two kinds of sucrose catabolism can be used. According to the phosphoenolpyruvate (PEP)-dependent phosphotransferase system ("PTS"), sucrose is transported into the microorganism and concomitantly phosphorylated to generate intracellular sucrose-6-phosphate which is hydrolysed to glucose-6-phosphate and fructose that are then involved in the central carbon metabolism of the cell. PTS can be encoded by scr or sac genes. According to non-phosphotransferase-dependent system ("non-PTS"), extracellular sucrose enters the cell with the aid of a proton symport transport system (sucrose permease) and, after transport, is hydrolysed by an invertase enzyme to glucose and fructose followed by phosphorylation. In this regard, the csc regulon consists of genes encoding the enzymes that are responsible for the non-PTS sucrose utilization.

During fermentation in the process of this invention, the oligosaccharide-producing microorganism is fed with sucrose that provides energy via glycolysis for growing, reproducing and maintaining its structure. In addition, the sucrose taken up by the cell provides, via sucrose catabolism, precursors for the synthesis of the activated sugar nucleotide(s) necessary for the glycosylation process that takes place in the cell. The internalized carbohydrate acceptor participates in the glycosyl transferase induced glycosylation reaction, in which a glycosyl residue of an activated nucleotide donor produced by the cell is transferred so that the acceptor is glycosylated. Optionally, when more than one glycosyl transferase is expressed by the cell, additional glycosylation reactions can occur resulting in the formation of the target oligosaccharide. Of course, the cell preferably lacks any enzyme activity which would degrade the oligosaccharide derivatives produced in the cell.

In a preferred realization of the process for making an oligosaccharide product, the sucrose utilization system is heterologous. This is the case when the microorganism, preferably a bacterium, more preferably an $E.$ $coli$, is a strain that is optimized for an industrially profitable transformation like oligosaccharide production, because such a strain generally has no ability to utilize sucrose. Therefore, a sucrose uptake cassette should be introduced, using an appropriate expression plasmid or via chromosome integration, in the sucrose minus cell to make it be sucrose plus. More preferably, the sucrose pathway genes comprise a PTS-dependent sucrose utilization system, and especially the source regulon is scr. Microorganisms having scr genes are for example $Salmonella$ ssp., $Klebsiella$ $pneumoniae,$ $Bacteroides$ $fragilis,$ $Vibrio$ $alginolyticus.$ The scr genes comprise the following: scrY, scrA, scrB, scrR and scrK. The gene scrA codes for the sucrose transport protein Enzyme II$^{scr}$ that provides intracellular sucrose-6-phosphate from extracellular sucrose via an active transport through the cell membrane and the concomitant phosphorylation. The sucrose specific ScrY porin (encoded by scrY) facilitate the sucrose diffusion through the outer membrane. The ScrB invertase enzyme (encoded by scrB) splits the accumulated sucrose-6-phosphate by hydrolysis to glucose-6-phosphate and fructose. Optionally, a fructokinase ScrK (encoded by scrK) phosphorylates fructose to fructose-6-phosphate, however the presence of this enzyme is not crucial because the fructose can be phosphorylated by other mechanisms owned by the cell. The repressor protein ScrR (encoded by scrR) negatively controls the expression of the scrYAB genes and is induced by sucrose or fructose.

In one embodiment, the heterologous scr genes are introduced into the microorganism using plasmids, for example by a two-plasmid system where one contains the scrA gene and the other does the scrB gene. The scrY, scrR and optionally the scrK gene can be carried by either plasmids. In a preferred embodiment, the heterologous scr genes are introduced into the genome of the microorganism, that is they are inserted in a certain site of the genome (genetic locus) of said microorganism or cell, preferably operably linked to one or more control sequence(s) that is recognized by the host cell.

Also preferably, the genes coding for the glycosyl transferases are also inserted in the genome of the host cell. In this regard, the preferred oligosaccharide producing cells of the invention are plasmid-free.

Also preferably, antibiotics are not added to the fermentation broth and neither during cell bank preparation and inoculum propagation in the process of some embodiments of this invention.

The carbohydrate acceptor to be glycosylated by the microorganism in the process of the invention can be a mono- or disaccharide selected from galactose, N-acetylglucosamine, a galactosylated monosaccharide, an N-acetylglucosaminylated monosaccharide, and glycosidic derivatives thereof defined above. All these carbohydrate derivatives can be easily taken up by a cell having a LacY permease by means of an active transport and accumulate in the cell before being glycosylated (WO 01/04341, Fort et al. $J.$ $Chem.$ $Soc.,$ $Chem.$ $Comm.$ 2558 (2005), EP-A-1911850, WO 2013/182206, WO 2014/048439). This is because the cell is able to transport these carbohydrate acceptors into the cell using its LacY permease, and the cell lacks any enzymes that could degrade these acceptors, especially LacZ. Preferably the cell has a deleted or deficient lacA gene on the lac operon.

According to another preferred embodiment, the lacI gene for the lac repressor is also deleted or deactivated in the microorganism. In the absence of the functioning repressor, no inducer is needed for any gene under the control of the promoter Plac.

According to one embodiment, the hlyE gene, coding for the toxin cytolysin A, is deleted or deactivated in order to eliminate the risk of unintended expression of the toxin and thus to obtain a safer manufacturing strain.

In one embodiment, if a glp promoter is used to express one or more recombinant genes in the microorganism or cell according to the invention (see above), the regulatory repressor gene glpR may be deleted or deactivated (see WO 2019/123324), which may result in a higher overall production of the product oligosaccharides, particularly HMOs.

According to one embodiment, the genetically modified cell used in the process of the invention, particularly a LacZ$^-$ $E.$ $coli$ cell, is cultured in an aqueous culture medium in the following phases:

(a) an exponential cell growth phase ensured by sucrose at least 12 hours, such as around 18 hours or 20-25 hours, and then (b) a second (feeding) phase with sucrose which is added continuously ensuring a limited cell growth that lasts until the sucrose and preferably most (e.g. at least 60%) of the lactose have been consumed which is preferably at least 35 hours, such as at least 45 hours, 50 to 70 hours, or up to about 130 hours.

During the feeding phase, the exogenous carbohydrate acceptor, preferably lactose, to be internalized by and glycosylated in the cell, can be added to the culture medium at once, sequentially or continuously. The acceptor can be added in this second phase as a pure solid/liquid or in a form of a concentrated aqueous solution or suspension. The oligosaccharide production takes place in this second phase and can take up to 6-7 days. Preferably, this feeding phase is performed under conditions allowing the production of a culture with a high cell density.

A feature of the process of some embodiments of this invention is that there is no need to change the carbon source and/or the energy source between the growth phase and the production phase of the microorganism.

Optionally, in the case that the cells are still in possession of the lactose repressor gene lacI, the process further comprises the addition of an inducer to the culture medium to induce the expression in the cell of enzyme(s) and/or of protein(s) involved in the transport of the acceptor and/or in the glycosylation of the internalized acceptor and/or in the biosynthesis of the activated sugar nucleotide donors. The inducer is preferably isopropyl β-D-thiogalactoside (IPTG) and is added to the culture medium in the beginning of the feeding phase. However, the use of inducer is not necessary if the cell is of LacI⁻ genotype.

It is believed that some embodiments of the microorganisms used in the process of invention and described above are highly stable under the process conditions of this invention described above. As a result, it is believed that these microorganisms can be used to produce oligosaccharides using sucrose as their carbon and energy sources at least at the same production rate as, and in a more reliable and reproducible manner than, microorganisms using glycerol and/or glucose as their carbon and/or energy sources. Beneficially, some embodiments of the genetically modified cells used in the process of the invention produce less carbohydrate by-products while the HMO titre and yield can be at least retained or even slightly increased, compared to the glucose or glycerol utilizing strains. The use of the sucrose strains is therefore beneficial as it facilitates the purification process. Furthermore, the HMOs made by the sucrose strains are extremely low in the sum of unspecified impurities. The reduced by-product formation provides a bigger upstream process optimisation potential, since the sucrose strain does not waste as much energy in the production. Additionally, the sucrose is more resistant to heat sterilization than e.g. monosaccharide carbon sources like glucose, and thus the HMOs produced by the sucrose strain do not contain such degradation by-products.

At the end of the fermentation process, the oligosaccharide product has accumulated both in the intra- and the extracellular matrix of the microorganism. The product has preferably been transported out of the cell to the supernatant in a passive way, i.e. it can diffuse outside across the cell membrane. This transport can be facilitated by one or more sugar efflux transporters in the cell, i.e. proteins that promote the effluence of sugar derivatives from the cell to the supernatant. The sugar efflux transporter(s) can be homologous or heterologous and can be overexpressed under the conditions of the fermentation to enhance the export of the oligosaccharide derivative produced. The specificity towards the sugar moiety of the product to be secreted can be altered by mutation of the cell by means of conventional recombinant DNA manipulation techniques and protein engineering. Preferably, the oligosaccharide accumulates in the extracellular matrix. Alternatively, the oligosaccharide can be transported out of the cell to the supernatant by permealizing the cell or disrupting the cell walls in a conventional manner.

The oligosaccharide product can then be separated in a conventional manner from the aqueous culture medium, in which it was made by the cell.

A first step of separating the oligosaccharide from the culture medium preferably involves separating the oligosaccharide from the microorganism which produced it. This preferably involves clarifying the culture medium to remove suspended particulates and contaminants, particularly cells, cell components, insoluble metabolites and debris produced by culturing the genetically modified microorganism. In this step, the aqueous culture medium, which contains the oligosaccharide product, can be clarified in a conventional manner. Preferably, the culture medium is clarified by centrifugation and/or microfiltration and/or ultrafiltration.

A second step of separating the oligosaccharide from the culture medium preferably involves removing substantially all the proteins, as well as peptides, amino acids, RNA and DNA and any endotoxins and glycolipids that could interfere with the subsequent separation step, from the aqueous culture medium, preferably after it has been clarified. In this step, proteins and related impurities can be removed from the culture medium in a conventional manner. For example, proteins and related impurities are removed from the culture medium by ultrafiltration, tangential flow high-performance filtration, tangential flow ultrafiltration, affinity chromatography, ion exchange chromatography, hydrophobic interaction chromatography and/or gel filtration (i.e., size exclusion chromatography), particularly by chromatography, more particularly by ion exchange chromatography or hydrophobic interaction chromatography. With the exception of size exclusion chromatography, proteins and related impurities are retained by a chromatography medium or a selected membrane, while the oligosaccharide product remains in the aqueous culture medium.

If desired, the oligosaccharide product in the aqueous culture medium can then be separated from sugar-like by-product(s) and from the culture medium, after proteins and related impurities have been removed from the culture medium. This can be suitably done by subjecting the culture medium to chromatographic separation. This separation can be carried out, in case of a neutral oligosaccharide product, in a chromatographic separation column(s), filled with a conventional cationic and/or anionic ion exchange resin. The acidic cationic ion exchange resin can be in monovalent or divalent cationic form and is preferably in $H^+$, $K^+$, $Na^+$, $Mg^{2+}$ or $Ca^{2+}$ form, particularly $Ca^{2+}$. The chromatographic separation can be carried out in a conventional manner at a pH of the solution of 2 to 9. The eluent used in the chromatographic separation is preferably water, especially demineralized water, but aqueous salt solutions can also be used. Alcohols, such as ethanol, and aqueous alcohol mixtures can also be used. Treatment with ion exchange resins removes charged particles and salts, too.

Optionally, at any phase of the separation of the oligosaccharide product from the culture medium, the aqueous solution containing said oligosaccharide can be treated with active charcoal, preferably to remove coloured bodies from the solution.

According to a preferred embodiment, the process of this invention for producing an oligosaccharide, preferably having a lactose unit at the reducing end or a glycoside thereof comprises the steps of:

(i) providing a genetically modified cell comprising
   a recombinant gene encoding a glycosyl transferase enzyme which is able to transfer the glycosyl residue of an activated sugar nucleotide to the internalized lactose or glycoside thereof,
   a biosynthetic pathway to the activated sugar nucleotide,
(ii) culturing the genetically modified cell in the presence of the exogenous lactose or glycoside thereof and sucrose inducing
   internalization of the exogenous lactose or glycoside thereof via an active transport mechanism by the genetically modified cell, and
   formation of the oligosaccharide having a lactose unit at the reducing end or a glycoside thereof from the internalized lactose or glycoside thereof by a glycosyl transfer mediated by the glycosyl transferase enzyme expressed by the cell,
(iii) isolating the oligosaccharide product from the cell, from the culture medium or from both,
characterized in that the cell also comprises a heterologous sucrose utilization system, preferably a PTS-dependent sucrose utilization system, especially where the source regulon is scr, to provide sucrose as a carbon source for biosynthesis of said activated sugar nucleotide by said cell.

The genetically modified cell, used in this preferred process, can have more than one recombinant gene, encoding more than one glycosyl transferase enzyme which is able to transfer the glycosyl residue of an activated sugar nucleotide to an internalized acceptor molecule or the previously glycosylated acceptor made by the same cell, so the oligosaccharide product is formed from the internalized acceptor by multiple glycosyl transfer mediated by multiple glycosyl transferases expressed by the cell. Accordingly, the resulting oligosaccharide product can be a glycosylated lactose or a glycoside thereof. The glycosylated lactose is preferably an N-acetyl-glucosaminylated, galactosylated, fucosylated and/or sialylated lactose. In order to produce these derivatives the cell comprises one or more recombinant genes encoding an N-acetyl-glucosaminyl transferase, a galactosyl transferase, a sialyl transferase and/or a fucosyl transferase, and also comprise a biosynthetic pathway to the corresponding activated sugar type nucleotides, that is UDP-GlcNAc, UDP-Gal, GDP-Fuc and/or CMP-sialic acid.

More preferably, the oligosaccharide product made by this process is characterized by formula 1

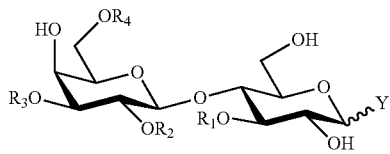

I wherein Y is OH or a non-sugar aglycon defined above, preferably OH, $R_1$ is fucosyl or H, $R_2$ is fucosyl or H, $R_3$ is selected from H, sialyl, N-acetyl-lactosaminyl and lacto-N-biosyl groups, wherein the N-acetyl-lactosaminyl group can carry a glycosyl residue comprising one or more N-acetyl-lactosaminyl and/or one or more lacto-N-biosyl groups; each of the N-acetyl-lactosaminyl and lacto-N-biosyl groups can be substituted with one or more sialyl and/or fucosyl residue, $R_4$ is selected from H, sialyl and N-acetyl-lactosaminyl groups optionally substituted with a glycosyl residue comprising one or more N-acetyl-lactosaminyl and/or one or more lacto-N-biosyl groups; each of the N-acetyl-lactosaminyl and lacto-N-biosyl groups can be substituted with one or more sialyl and/or fucosyl residue, provided that at least one of the $R_1$, $R_2$, $R_3$ and $R_4$ groups is different from H.

Even more preferably, the compound of formula 1 made by this process can be characterized by formula 1a, 1b or 1C

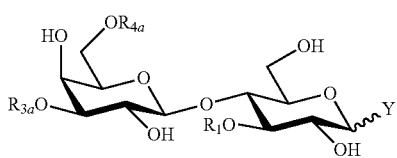

Ia

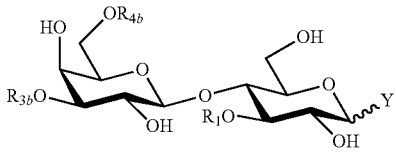

Ib

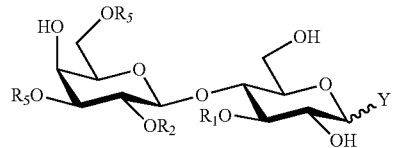

Ic wherein Y, $R_1$ and $R_2$ are as defined above, preferably OH, $R_{3a}$ is an N-acetyl-lactosaminyl group optionally substituted with a glycosyl residue comprising one N-acetyl-lactosaminyl and/or one lacto-N-biosyl group; each of the N-acetyl-lactosaminyl and lacto-N-biosyl groups can be substituted with one or more sialyl and/or fucosyl residue, $R_{4a}$ is H or an N-acetyl-lactosaminyl group optionally substituted with a lacto-N-biosyl group; each of the N-acetyl-lactosaminyl and lacto-N-biosyl groups can be substituted with one or more sialyl and/or fucosyl residue, $R_{3b}$ is a lacto-N-biosyl group optionally substituted with one or more sialyl and/or fucosyl residue(s), $R_{4b}$ is H or an N-acetyl-lactosaminyl group optionally substituted with one or two N-acetyl-lactosaminyl and/or one lacto-N-biosyl groups; each of the N-acetyl-lactosaminyl and lacto-N-biosyl groups can be substituted with one or more sialyl and/or fucosyl residues, $R_5$ is, independently, H or sialyl, and wherein at least one of $R_1$, $R_2$ or $R_5$ is not H.

Still more preferably, the compounds according to formulae 1a or 1b made by this process are characterized in that:

the N-acetyl-lactosaminyl group in the glycosyl residue of $R_{3a}$ is attached to another N-acetyl-lactosaminyl group with a 1-3 interglycosidic linkage, the lacto-N-biosyl group in the glycosyl residue of $R_{3a}$ is attached to the N-acetyl-lactosaminyl group with a 1-3 interglycosidic linkage, the lacto-N-biosyl group in the glycosyl residue of $R_{4a}$ is attached to the N-acetyl-lactosaminyl group with a 1-3 interglycosidic linkage, the N-acetyl-lactosaminyl group in the glycosyl residue of $R_{4b}$ is attached to another N-acetyl-lactosaminyl group with a 1-3 or a 1-6 interglycosidic linkage, the lacto-N-biosyl group in the glycosyl residue of $R_{4b}$ is attached to the N-acetyl-lactosaminyl group with a 1-3 interglycosidic linkage.

Yet more preferably, the compounds according to formulae 1a, 1b and 1c made by the process are human milk oligosaccharides (when Y is OH) or glycosides thereof (when Y is non-sugar aglycon).

The preferred compounds of formula 1a made by the process are selected from lacto-N-neotetraose, para-lacto-N-hexaose, para-lacto-N-neohexaose, lacto-N-neohexaose, para-lacto-N-octaose, lacto-N-neooctaose and glycosides thereof, all of which can optionally be substituted with one or more sialyl and/or fucosyl residue. The preferred compounds of formula 1b made by the process is selected from lacto-N-tetraose, lacto-N-hexaose, lacto-N-octaose, isolacto-N-octaose, lacto-N-decaose, lacto-N-neodecaose and glycosides thereof, all of them can optionally be substituted with one or more sialyl and/or fucosyl residue.

Particularly preferred compounds of formula 1a or 1b are characterized in that:
the fucosyl residue attached to the N-acetyl-lactosaminyl and/or the lacto-N-biosyl group is linked to
the galactose of the lacto-N-biosyl group with 1-2 interglycosidic linkage and/or
the N-acetyl-glucosamine of the lacto-N-biosyl group with 1-4 interglycosidic linkage and/or
the N-acetyl-glucosamine of the N-acetyl-lactosaminyl group with 1-3 interglycosidic linkage,
the sialyl residue attached to the N-acetyl-lactosaminyl and/or the lacto-N-biosyl group is linked to
the galactose of the lacto-N-biosyl group with 2-3 interglycosidic linkage and/or
the N-acetyl-glucosamine of the lacto-N-biosyl group with 2-6 interglycosidic linkage and/or
the galactose of the N-acetyl-lactosaminyl group with 2-6 interglycosidic linkage.

According to the most preferred aspect, the compounds of subformulae 1a, 1b or 1c are selected from the group of: 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I, FDS-LNT II and their glycosides, or salts thereof. The glycosides can be alpha or beta-anomers, but preferably beta-anomers.

One preferred carbohydrate acceptor, exogenously added to the culture medium, is lactose, and the preferred oligosaccharide product is a human milk oligosaccharide (HMO). The HMOs consist of a lactose unit at the reducing end and one or more from the following monosaccharide units: N-acetyl-glucosamine, galactose, fucose and sialic acid (see Urashima et al.: *Milk Oligosaccharides*, Nova Biomedical Books, New York, 2011, ISBN: 978-1-61122-831-1; Chen *Adv. Carbohydr. Chem. Biochem.* 72, 113 (2015)). In order to produce HMOs the cell then comprises one or more recombinant genes encoding β-1,3-N-acetyl-glucosaminyl transferase, β-1,6-N-acetyl-glucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and/or α-1,4 fucosyl transferase, and also comprise a biosynthetic pathway to the corresponding activated sugar type nucleotides, that is UDP-GlcNAc, UDP-Gal, GDP-Fuc and/or CMP-sialic acid.

According to a preferred embodiment, the process of the invention relates to the production of neutral (non-acidic) HMOs. The neutral HMOs do not contain sialic acid residue in their structure and therefore can be non-fucosylated neutral HMOs (referred to as N-acetylated HMOs or core HMOs) and fucosylated HMOs. The N-acetylated HMOs has only three types of monosaccharide in their structure: glucose, galactose and N-acetyl-glucosamine, and the N-acetylated HMOs are preferably selected from the group consisting of lacto-N-neotetraose, para-lacto-N-hexaose, para-lacto-N-neohexaose, lacto-N-neohexaose, para-lacto-N-octaose, lacto-N-neooctaose, lacto-N-tetraose, lacto-N-hexaose, lacto-N-octaose, iso-lacto-N-octaose, lacto-N-decaose and lacto-N-neodecaose, more preferably lacto-N-neotetraose, lacto-N-tetraose, lacto-N-hexaose, para-lacto-N-hexaose, para-lacto-N-neohexaose and lacto-N-neohexaose. The group of fucosylated neutral HMOs encompasses N-acetylated HMOs disclosed above that are fucosylated and fucosylated lactoses (2'-FL, 3-FL, DFL).

According, the process, in a preferred embodiment, relates to the production of neutral HMOs comprising:
(i) providing a genetically modified *E. coli* cell comprising:
(ia)—a recombinant gene encoding a N-acetyl-glucosaminyl transferase enzyme which is able to transfer the GlcNAc of UDP-GlcNAc to the internalized lactose or to an intermediate in the biosynthetic pathway to said neutral HMO from lactose, and one or more genes encoding a biosynthetic pathway to UDP-GlcNAc; and/or
a recombinant gene encoding a fucosyl transferase enzyme which is able to transfer the fucosyl residue of GDP-Fuc to the internalized lactose or to an intermediate in the biosynthetic pathway to said neutral HMO from lactose, and one or more genes encoding a biosynthetic pathway to GDP-Fuc,
(ib)—optionally a recombinant gene encoding a galactosyl transferase enzyme which is able to transfer the galactosyl residue of UDP-Gal to an intermediate in the biosynthetic pathway to said neutral HMO from lactose, and one or more genes encoding a biosynthetic pathway to UDP-Gal,
(ii) culturing the genetically modified *E. coli* cell in the presence of exogenous lactose and sucrose, thereby inducing:
internalization of the exogenous lactose, and
formation, within the cell, of neutral HMO, and then
(iii) separating the neutral HMO from the cell, from the culture medium or from both,
characterized in that the cell also comprises a heterologous PTS-dependent sucrose utilization system to provide sucrose as a carbon source, as well as an energy source, for biosynthesis of UDP-GlcNAc and/or GDP-Fuc, and optionally UDP-Gal by the cell, and as energy source for making said neutral HMO.

The heterologous PTS-dependent sucrose utilization system preferably comprises scr genes, more preferably scrY, scrA, scrB and scrR, and particularly does not contain scrK.

According to another preferred embodiment, the process of this invention for producing an N-acetylated HMO, preferably of 3-6 monosaccharide units, comprises the steps of:
(i) providing a genetically modified *E. coli* cell comprising:
a recombinant gene encoding a N-acetyl-glucosaminyl transferase enzyme which is able to transfer the GlcNAc of UDP-GlcNAc to the internalized lactose or to an intermediate in the biosynthetic pathway to said N-acetylated HMO from lactose,
optionally a recombinant gene encoding a galactosyl transferase enzyme which is able to transfer the galactosyl residue of UDP-Gal to the N-acetyl-glucosaminylated lactose to an intermediate in the biosynthetic pathway to said N-acetylated HMO from lactose, and
one or more genes encoding a biosynthetic pathway to UDP-GlcNAc and optionally to UDP-Gal,
(ii) culturing the genetically modified *E. coli* cell in the presence of exogenous lactose and sucrose, thereby inducing:
internalization of the exogenous lactose, and
formation, within the cell, of an N-acetylated HMO, and then
(iii) separating the N-acetylated HMO from the cell, from the culture medium or from both, characterized in that the cell also comprises a heterologous PTS-dependent sucrose utilization system to provide sucrose as a carbon source, as well as an energy source, for biosynthesis of UDP-GlcNAc and optionally UDP-Gal by the cell, and as energy source for making said N-acetylated HMO.

The heterologous PTS-dependent sucrose utilization system preferably comprises scr genes, more preferably scrY, scrA, scrB and scrR, and particularly does not contain scrK.

If the N-acetyl-glucosaminyl transferase is a β-1,3-N-acetyl-glucosaminyl transferase and no recombinant gene encoding a galactosyl transferase is present in the cell, the product is preferably lacto-N-triose II, and if a β-1,3- or a β-1,4-galactosyl transferase is also present in the cell, the product is preferably LNT or LNnT, respectively.

According to another preferred embodiment, the process of this invention for producing a fucosylated N-acetylated HMO, preferably LNFP-I, LNFP-II, LNFP-III, LNFP-V, LNFP-VI, LNDFH-I, LNDFH-II or LNDFH-III, comprises the steps of:

(i) providing a genetically modified *E. coli* cell comprising:
   a recombinant gene encoding a N-acetyl-glucosaminyl transferase enzyme which is able to transfer the GlcNAc of UDP-GlcNAc to the internalized lactose or to an intermediate in the biosynthetic pathway to said fucosylated N-acetylated HMO from lactose, and one or more genes encoding a biosynthetic pathway to UDP-GlcNAc;
   a recombinant gene encoding a fucosyl transferase enzyme which is able to transfer the fucosyl residue of GDP-Fuc to the internalized lactose or to an intermediate in the biosynthetic pathway to said fucosylated N-acetylated HMO from lactose, and one or more genes encoding a biosynthetic pathway to GDP-Fuc, and
   a recombinant gene encoding a galactosyl transferase enzyme which is able to transfer the galactosyl residue of UDP-Gal to an intermediate in the biosynthetic pathway to said fucosylated N-acetylated HMO from lactose, and one or more genes encoding a biosynthetic pathway to UDP-Gal, (ii) culturing the genetically modified *E. coli* cell in the presence of exogenous lactose and sucrose, thereby inducing:
   internalization of the exogenous lactose, and
   formation, within the cell, of the fucosylated N-acetylated HMO, and then (iii) separating the fucosylated N-acetylated HMO from the cell, from the culture medium or from both, characterized in that the cell also comprises a heterologous PTS-dependent sucrose utilization system to provide sucrose as a carbon source, as well as an energy source, for biosynthesis of UDP-GlcNAc, GDP-Fuc and optionally UDP-Gal by the cell, and as energy source for making said fucosylated N-acetylated HMO.

The heterologous PTS-dependent sucrose utilization system preferably comprises scr genes, more preferably scrY, scrA, scrB and scrR, and particularly does not contain scrK.

According to yet another preferred embodiment, the process of this invention for producing a fucosylated lactose, preferably 2'-FL, 3-FL or DFL, comprises the steps of:

(i) providing a genetically modified *E. coli* cell comprising:
   a recombinant gene encoding a fucosyl transferase enzyme which is able to transfer the fucosyl residue of GDP-Fuc to the internalized lactose, and
   one or more genes encoding a biosynthetic pathway to GDP-Fuc, (ii) culturing the cell in the presence of exogenous lactose and sucrose, thereby inducing:
   internalization of the exogenous lactose, and
   formation of the fucosylated lactose, and then (iii) separating the fucosylated lactose product from the cell, from the culture medium or from both, characterized in that the cell also comprises a heterologous PTS-dependent sucrose utilization system to provide sucrose as a carbon source, as well as an energy source, for biosynthesis of GDP-Fuc by the cell, and as energy source for making said fucosylated lactose.

The heterologous PTS-dependent sucrose utilization system preferably comprises scr genes, more preferably scrY, scrA, scrB and scrR, and particularly does not contain scrK.

If the fucosyl transferase is an α-1,2-fucosyl transferase, the product is preferably 2'-fucosyllactose (2'-FL), if the fucosyl transferase is an α-1,3-fucosyl transferase, the product is preferably 3-fucosyllactose (3-FL), and if both α-1,2- and α-1,3-fucosyl transferases are expressed in the cell, the product is preferably difucosyllactose (DFL).

According to still another preferred embodiment, the process of this invention for producing a sialylated HMO, preferably of 3-5 monosaccharide units, comprises the steps of:

(i) providing a genetically modified *E. coli* cell comprising:
   a recombinant gene encoding a sialyl transferase enzyme which is able to transfer the sialyl residue of CMP-sialic acid to the internalized lactose or to an intermediate in the biosynthetic pathway to said sialylated HMO from lactose, and
   one or more genes encoding a biosynthetic pathway to CMP-sialic acid, (ii) culturing the genetically modified *E. coli* cell in the presence of exogenous lactose and sucrose, thereby inducing:
   internalization of the exogenous lactose, and
   formation of a sialylated HMO, and then (iii) separating the sialylated HMO from the cell, from the culture medium or from both, characterized in that the cell also comprises a heterologous PTS-dependent sucrose utilization system to provide sucrose as a carbon source, as well as an energy source, for biosynthesis of CMP-sialic acid by the cell, and as energy source for making said sialylated HMO.

The heterologous PTS-dependent sucrose utilization system preferably comprises scr genes, more preferably scrY, scrA, scrB and scrR, and particularly does not contain scrK.

If the sialyl transferase is an α-2,3-sialyl transferase, the product is preferably 3'-sialyllactose, and if the sialyl transferase is an α-2,6-sialyl transferase, the product is preferably 6'-sialyllactose.

According to another preferred embodiment, the process of this invention for producing a fucosylated and sialylated HMO, preferably of 3-5 monosaccharide units, comprises the steps of:

(i) providing a genetically modified *E. coli* cell comprising:
   a recombinant gene encoding a sialyl transferase enzyme which is able to transfer the sialyl residue of CMP-sialic acid to the internalized lactose or to an intermediate in the biosynthetic pathway to said fucosylated and sialylated HMO from lactose,
   a recombinant gene encoding a fucosyl transferase enzyme which is able to transfer the fucosyl residue of GDP-Fuc to the internalized lactose or to an intermediate in the biosynthetic pathway to said fucosylated and sialylated HMO from lactose, and one or more genes encoding a biosynthetic pathway to CMP-sialic acid and GDP-Fuc, (ii) culturing the genetically modified *E. coli* cell in the presence of exogenous lactose and sucrose, thereby inducing:

internalization of the exogenous lactose, and formation of a sialyl-fucosyl-lactose, and then (iii) separating the fucosylated and sialylated HMO from the cell, from the culture medium or from both, characterized in that the cell also comprises a heterologous PTS-dependent sucrose utilization system to provide sucrose as a carbon source, as well as an energy source, for biosynthesis of CMP-sialic acid and GDP-Fuc by the cell, and as energy source for making said fucosylated and sialylated HMO.

The heterologous PTS-dependent sucrose utilization system preferably comprises scr genes, more preferably scrY, scrA, scrB and scrR, and particularly does not contain scrK.

If the sialyl transferase is an α-2,3-sialyl transferase and the fucosyl transferase is an α-1,3-fucosyl transferase, the product is preferably 3'-sialyl-3-fucosyllactose.

According to another preferred embodiment, the process of this invention for producing a fucosylated LNT or LNnT, comprises the steps of:

(i) providing a genetically modified *E. coli* cell comprising:

a recombinant gene encoding a N-acetyl-glucosaminyl transferase enzyme which is able to transfer the GlcNAc of UDP-GlcNAc to the internalized lactose to make lacto-N-triose, a recombinant gene encoding a galactosyl transferase enzyme which is able to transfer the galactosyl residue of UDP-Gal to the lacto-N-triose to make LNT or LNnT, a recombinant gene encoding a fucosyl transferase enzyme which is able to transfer the fucosyl residue of GDP-Fuc to the LNT or LNnT, one or more genes encoding a biosynthetic pathway to GDP-Fuc one or more genes encoding a biosynthetic pathway to UDP-GlcNAc and to UDP-Gal, (ii) culturing the genetically modified *E. coli* cell in the presence of exogenous lactose and sucrose, thereby inducing:

internalization of the exogenous lactose, and formation of a fucosylated LNT or LNnT, and then (iii) separating the fucosylated LNT or LNnT from the cell, from the culture medium or from both, characterized in that the cell also comprises a heterologous PTS-dependent sucrose utilization system to provide sucrose as a carbon source, as well as an energy source, for biosynthesis of UDP-GlcNAc, UDP-Gal and GDP-Fuc by the cell, and as energy source for making said fucosylated LNT or LNnT.

The heterologous PTS-dependent sucrose utilization system preferably comprises scr genes, more preferably scrY, scrA, scrB and scrR, and particularly does not contain scrK.

A second aspect of the invention relates to providing a genetically modified microorganism that can internalize sucrose and a carbohydrate acceptor, which is not sucrose, preferably lactose, or a glycoside thereof, into said microorganism and that comprises:

a recombinant gene encoding a glycosyl transferase which can transfer a glycosyl residue of an activated sugar nucleotide to the acceptor within the microorganism, a biosynthetic pathway for making the activated sugar nucleotide from sucrose, and one or more genes encoding a heterologous PTS-dependent sucrose utilization system, preferably scr genes, so that said cell can use sucrose as a carbon source, preferably the main carbon source, more preferably the sole carbon source, for making said activated sugar nucleotide and as an energy source, preferably the main energy source, more preferably the sole energy source, thereby making an oligosaccharide or a glycoside thereof comprising the internalized carbohydrate acceptor in its structure.

The aglycon moieties of the glycosides of the internalized carbohydrate acceptors or the oligosaccharide products are disclosed in the first aspect.

The genetically modified microorganism or cell of this invention can be selected from the group consisting of bacteria and yeasts, preferably a bacterium. Bacteria are preferably selected from the group of: *Escherichia coli, Bacillus* spp. (e.g. *Bacillus subtilis*), *Campylobacter pylori, Helicobacter pylori, Agrobacterium tumefaciens, Staphylococcus aureus, Thermophilus aquaticus, Azorhizobium caulinodans, Rhizobium leguminosarum, Neisseria gonorrhoeae, Neisseria meningitis, Lactobacillus* spp., *Lactococcus* spp., *Enterococcus* spp., *Bifidobacterium* spp., *Sporolactobacillus* spp., *Micromomospora* spp., *Micrococcus* spp., *Rhodococcus* spp., *Pseudomonas*, among which *E. coli* is preferred.

Further in accordance with some embodiments of this invention, the microorganism or cell, preferably an *E. coli* cell, is genetically modified so that there is at least one alteration in its DNA sequence. The alteration can result in a change in the original characteristics of the wild type cell, e.g. the modified cell is able to perform additional chemical transformation due to the introduced new genetic material that encodes the expression of an enzymes not being in the wild type cell, or is not able to carry out transformation like degradation due to removal or deactivation of gene/genes. In this regard, a genetically modified cell contains at least one artificial alteration in its genome compared to its naturally occurring (wild type) variant. By the alteration, either a nucleic acid construct is added to the cell by way of integration into the genome or by addition via plasmid, or a nucleic acid sequence is deleted from or changed in the genome of the cell. Whatever is the case, the so-transformed cell has a genotype that is different from that before the alteration and, therefore, the modified cell shows modified feature(s). Preferably, the genetically modified cell can perform at least one additional or altered biochemical reaction, when cultured or fermented, due to the introduction of a heterologous nucleic acid sequence or the modification of a native nucleic acid sequence that encodes an enzyme that is not expressed in the wild type cell, or the genetically modified cell cannot perform a biochemical reaction due to the deletion, addition or modification of a nucleic acid sequence that encodes an enzyme found in the wild type cell. The genetically modified cell can be constructed by well-known, conventional genetic engineering techniques (e.g. Green and Sambrook: *Molecular Cloning: A laboratory Manual*, 4$^{th}$ ed., Cold Spring Harbor Laboratory Press (2012); *Current protocols in molecular biology* (Ausubel et al. eds.), John Wiley and Sons (2010)). The terms "host cell", "recombinant microorganism or cell" or "genetically modified microorganism or cell" are used interchangeably to designate such constructs.

The term "promoter" means a nucleic acid sequence involved in the binding of RNA polymerase to initiate transcription of an operably linked gene, wherein the gene includes a coding DNA sequence and other (non-coding) sequences, e.g. the 5'-untranslated region (5'-UTR) located upstream of the coding sequence, which comprises a ribosomal binding site. A promoter in some embodiments of this invention is an isolated DNA sequence, i.e. not an integrated DNA fragment of the genomic DNA. The nucleotide sequence of a promoter corresponds to, or have at least 80% identity, preferably 90-99.9% identity with the nucleotide sequence of a fragment of bacterial genomic DNA that is regarded as promoter region of a gene, e.g. a promoter region of a glp operon or lac operon of *E. coli*. By "operon" is meant a functioning unit of genomic DNA containing a cluster of genes under the control of a single promoter. By "glp operon" is meant a cluster of genes involved in the respiratory metabolism of glycerol of bacteria. Preferably, a glp operon promoter sequence comprised in a DNA construct corresponds to or has at least 80% identity, preferably 90-99.9% identity with the nucleotide sequence of a fragment of the genomic DNA regarded as a promoter region of the corresponding glp operon of *E. coli*; in particular, the isolated sequence of a promoter of a glp operon of some embodiments of the invention corresponds to, or has said percent of identity with a fragment of the genomic sequence upstream the sequence having GenBank ID: EG10396 (glpFKX), EG10391 (glpABC), EG10394 (glpD), EG10401 (glpTQ). The *E. coli* genome is referred herein to the complete genomic DNA sequence of *E coli* K-12 MG1655 (GenBank ID:U00096.3).

In some embodiments, a promoter of the glp operon is operably linked to the heterologous glycosyl transferase genes and/or the heterologous scr genes. Preferably, those genes are expressed under a glpF promoter (WO 2019/123324, the content of which is incorporated herein by reference).

The genetically modified microorganism or cell of this invention is able to transport the exogenous carbohydrate acceptor, preferably lactose, into the cell for glycosylation to produce a foreign oligosaccharide of interest, preferably without adversely affecting the basic functions of the cell or destroying its integrity. In one embodiment, the transport takes place via a passive mechanism, during which the exogenous acceptor diffuses passively across the plasma membrane of the cell. Diffusion of the acceptor into the microorganism is a function of the concentration differences between the fermentation broth and the extra- and intracellular space of the cell with respect to the acceptor, whereby the acceptor passes from the place of higher concentration to the place of lower concentration. In another embodiment, the acceptor is internalized with the aid of an active transport. In such a case, the genetically modified microorganism contains transporter proteins, called permeases, which act as enzymes and with which the microorganism is able to admit exogenous substances and to concentrate them in the cytoplasm. Specifically, lactose permease (LacY) acts specifically on galactose, simple galactosyl disaccharides such as lactose and their glycosides. The specificity towards the sugar moiety of the exogenous carbohydrate acceptor to be internalized can be altered by mutation of the microorganism by means of conventional recombinant DNA manipulation techniques. In a preferred embodiment, the internalization of exogenous lactose or its derivative takes place via an active transport mechanism mediated by a lactose permease. The genetically modified microorganism preferably lacks any enzyme activity (such as LacZ) that would degrade the acceptor. Likewise, the microorganism is not able to hydrolyze or degrade the oligosaccharide product or any oligosaccharide intermediate in the biosynthetic pathway to the oligosaccharide product.

Moreover, the genetically modified cell of the invention comprises one or more endogenous or recombinant genes encoding one or more glycosyl transferase enzymes that are able to transfer the glycosyl residue of an activated sugar nucleotide to the internalized acceptor. The gene or an equivalent DNA sequence thereof, if it is recombinant, can be introduced into the cell by conventional techniques, e.g. using an expression vector or by chromosomal integration. The origin of the heterologous nucleic acid sequence can be any animal (including human) or plant, eukaryotic cells such as those from *Saccharomyces cerevisae, Saccharomyces pombe, Candida albicans* or from algae, prokaryotic cells such as those originated from *E. coli, Bacteroides fragilis, Photobacterium* sp., *Bacillus subtilis, Campylobacter pylori, Helicobacter pylori, Agrobacterium tumefaciens, Staphylococcus aureus, Thermophilus aquaticus, Azorhizobium caulinodans, Rhizobium leguminosarum, Rhizobium meliloti, Neisseria gonorrhoeae* and *Neisseria meningitidis,* or virus. The glycosyl transferase enzyme/enzymes encoded and expressed by the gene(s) or equivalent DNA sequence(s) are preferably glucosyl transferases, galactosyl transferases, N-acetylglucosaminyl transferases, N-acetylgalactosaminyl transferases, glucuronosyl transferases, xylosyl transferases, mannosyl transferases, fucosyl transferases, sialyl transferases and the like. In a preferred embodiment, the glycosyl transferases are selected from the group consisting of β-1,3-N-acetylglucosaminyl-transferase, β-1,6-N-acetylglucosaminyl-transferase, β-1,3-galactosyl-transferase, β-1,4-galactosyl-transferase, β-1,3-N-acetylgalactosaminyl-transferase, β-1,3-glucuronosyl-transferase, α-2,3-sialyl-transferase, α-2,6-sialyl-transferase, α-2,8-sialyl-transferase, α-1,2-fucosyl-transferase, α-1,3-fucosyl-transferase and α-1,4-fucosyl-transferase. More preferably, the glycosyl transferases are selected from β-1,3-N-acetylglucosaminyl transferase, β-1,6-N-acetylglucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and α-1,4 fucosyl transferase, that is from those involved in the construction of HMO core structures as well as fucosylated and/or sialylated HMOs and its glycosidic derivatives, wherein the aglycon is a moiety defined above at the group of carbohydrate acceptors. The genes encoding the above-mentioned transferases have been described in the literature.

The genetically modified microorganism or cell of the invention is capable of producing an oligosaccharide from the internalized precursor/acceptor which is preferably lactose. Said cell possesses enzymatic activity that is necessary for synthesizing an oligosaccharide, from an internalized mono- or disaccharide, or a glycoside thereof, via consecutive glycosylation steps, wherein the internalized acceptor, e.g. lactose, is glycosylated, in a first glycosylation step, to a trisaccharide, then that trisaccharide is glycosylated, in a second glycosylating step, to a tetrasaccharide, and so forth. The glycosylation steps are mediated by respective glycosyl transferases.

In the glycosyl transferase mediated glycosylation processes, activated sugar nucleotides serve as donors, and the glycosyl transferase in question transfers a monosaccharide of an appropriate donor molecule to the acceptor molecule. Each activated sugar nucleotide generally comprises a phosphorylated glycosyl residue attached to a nucleoside, and the specific glycosyl transferase enzyme accepts only the specific sugar nucleotide. Thus, preferably the following activated sugar nucleotides are involved in the glycosyl transfer: UDP-Glc, UDP-Gal, UDP-GlcNAc, UDP-GalNAc, UDP-glucuronic acid, UDP-Xyl, GDP-Man, GDP-Fuc and CMP-sialic acid, particularly those selected from the group consisting of UDP-Gal, UDP-GlcNAc, GDP-Fuc and CMP-sialic acid.

The genetically modified microorganism of this invention possesses a biosynthetic pathway to the above mentioned activated sugar nucleotides, that is, it has one or more sets of genes encoding one or more enzymes capable of the synthesis of one or more activated glycosyl nucleotides, ready for glycosylation in glycosyl transferase mediated reaction in the cell, when cultured. The sets of genes are either naturally present in the cell or introduced into the cell by means of recombinant DNA manipulation techniques. The production of the activated glycosyl nucleotides by the cell takes place under the action of enzymes involved in the biosynthetic pathway of that respective sugar nucleotide stepwise reaction sequence starting from a carbon source (for a review for monosaccharide metabolism see e.g. H. H. Freeze and A. D. Elbein: *Chapter 4: Glycosylation precursors*, in: Essentials of Glycobiology, $2^{nd}$ edition (Eds. A. Varki et al.), Cold Spring Harbour Laboratory Press (2009)).

It is emphasized that the production of the activated sugar nucleotides by the genetically modified microorganism via its own biosynthetic pathway is advantageous compared to in vitro versions of transfer glycosylation, as it avoids using the very expensive sugar nucleotide type donors added exogenously, hence the donors are formed by the cell in situ and the phosphatidyl nucleoside leaving groups are recycled in the cell.

In addition, the microorganism of the invention comprises genes encoding a sucrose utilization system, that is the cell has a capability to catabolically utilize sucrose as a carbon source, as well as an energy source. The system that enables the cell to utilize sucrose can be one normally found in the gene pool of that cell but preferably is a heterologous system (i.e. derived from a different organism and transferred to the host cell by conventional recombinant DNA manipulation techniques). Typically, two kinds of sucrose catabolism can be used. According to the phosphoenolpyruvate (PEP)-dependent phosphotransferase system ("PTS"), sucrose is transported into the microorganism and concomitantly phosphorylated to generate intracellular sucrose-6-phosphate which is hydrolysed to glucose-6-phosphate and fructose that are then involved in the central carbon metabolism of the cell. PTS can be encoded by scr or sac genes. According to non-phosphotransferase-dependent system ("non-PTS"), extracellular sucrose enters the cell with the aid of a proton symport transport system (sucrose permease) and, after transport, is hydrolysed by an invertase enzyme to glucose and fructose followed by phosphorylation. In this regard, the csc regulon consists of genes encoding the enzymes that are responsible for the non-PTS sucrose utilization.

In a preferred embodiment, the sucrose utilization system is heterologous. This is the case when the microorganism, preferably a bacterium, more preferably an *E. coli*, is a strain that is optimized for an industrially profitable transformation like oligosaccharide production, because such a strain generally has no ability to utilize sucrose. Therefore, a sucrose uptake cassette should be introduced, using an appropriate expression plasmid or via chromosome integration, in the sucrose minus cell to make it be sucrose plus. More preferably, the sucrose pathway genes comprise a PTS-dependent sucrose utilization system, and especially the source regulon is scr. Microorganisms having scr genes are for example *Salmonella* ssp., *Klebsiella pneumoniae, Bacteroides fragilis, Vibrio alginolyticus*.

The scr genes comprise the following: scrY, scrA, scrB, scrR and scrK. The gene scrA codes for the sucrose transport protein Enzyme II$^{scr}$ that provides intracellular sucrose-6-phosphate from extracellular sucrose via an active transport through the cell membrane and the concomitant phosphorylation. The sucrose specific ScrY porin (encoded by scrY) facilitate the sucrose diffusion through the outer membrane. The ScrB invertase enzyme (encoded by scrB) splits the accumulated sucrose-6-phosphate by hydrolysis to glucose-6-phosphate and fructose. Optionally, a fructokinase ScrK (encoded by scrK) phosphorylates fructose to fructose-6-phosphate, however the presence of this enzyme is not crucial because the fructose can be phosphorylated by other mechanisms owned by the cell. The repressor protein ScrR (encoded by scrR) negatively controls the expression of the scrYAB genes and is induced by sucrose or fructose.

In one embodiment, the heterologous scr genes are introduced into the microorganism using plasmids, for example by a two-plasmid system where one contains the scrA gene and the other does the scrB gene. The scrY, scrR and optionally the scrK gene can be carried by either plasmids.

In a preferred embodiment, the heterologous scr genes are introduced into the genome of the microorganism, that is they are chromosomally integrated by insertion in a certain site of the genome (genetic locus) of said microorganism or cell, preferably operably linked to one or more control sequence(s) that is recognized by the host cell.

Also preferably, the genes coding for the glycosyl transferases are also inserted in the genome of the host cell (that is, chromosomally integrated).

Also preferably, if one or more recombinant genes involved in the biosynthetic pathway to the activated sugar type nucleotides, preferably to UDP-GlcNAc, UDP-Gal, GDP-Fuc and/or CMP-sialic acid, necessary for the production of the oligosaccharide, preferably the HMO, are present in the genetically modified cell of the invention, it is (they are) also inserted in the genome of the host cell.

In this regard, the most preferred oligosaccharide producing cells of the invention are plasmid-free.

The control sequences or promoters operably linked to heterologous DNA sequences encoding the glycosyl transferases necessary for making the oligosaccharide product or the proteins necessary for the sucrose uptake can be any suitable promoter. In some embodiments, a promoter of the glp operon is used, preferably glpF or its variant (WO 2019/123324, the content of which is incorporated herein by reference).

The carbohydrate acceptor to be glycosylated by the microorganism of the invention can be a mono- or disaccharide selected from galactose, N-acetyl-glucosamine, a galactosylated monosaccharide, an N-acetyl-glucosaminylated monosaccharide, and glycosidic derivatives thereof defined above. All these carbohydrate derivatives can be easily taken up by a cell having a LacY permease by means of an active transport and accumulate in the cell before being glycosylated (WO 01/04341, Fort et al. *J. Chem. Soc., Chem. Comm.* 2558 (2005), EP-A-1911850, WO 2013/182206, WO 2014/048439). This is because the cell is able to transport these carbohydrate acceptors into the cell using its LacY permease, and the cell lacks any enzymes that could degrade these acceptors, especially LacZ. Preferably the cell has a deleted or deficient lacA gene on the lac operon.

According to another preferred embodiment, the lacI gene for the lac repressor is also deleted or deactivated in the microorganism. In the absence of the functioning repressor, no inducer is needed for expressing any gene under the control of the promoter Plac.

According to one embodiment, the hlyE gene, coding for the toxin cytolysin A, is deleted or deactivated in order to eliminate the risk of unintended expression of the toxin and thus to obtain a safer manufacturing strain.

In one embodiment, if a glp promoter is used to express one or more recombinant genes in the microorganism or cell according to the invention (see above), the regulatory repressor gene glpR may be deleted or deactivated (WO 2019/123324), which may result in a higher overall production of the product oligosaccharides, particularly HMOs.

It is believed that the microorganisms of invention described above are highly stable under the process conditions of this invention described above. As a result, it is believed that these microorganisms can be used to produce oligosaccharides using sucrose as their carbon and energy sources at least at the same production rate as, and in a more reliable and reproducible manner than, like microorganisms using glycerol and/or glucose as their carbon and/or energy sources. Beneficially, the genetically modified cells used in the process of the invention produce less carbohydrate by-products while the HMO titre and yield can be at least retained or even slightly increased, compared to the glucose or glycerol utilizing strains. The use of the sucrose strains is therefore beneficial as it facilitates the purification process. Furthermore, the HMOs made by the sucrose strains are extremely low in the sum of unspecified impurities. The reduced by-product formation provides a bigger upstream process optimisation potential, since the sucrose strain does not waste as much energy in the production. Additionally, the sucrose is more resistant to heat sterilization than e.g. monosaccharide carbon sources like glucose, and thus the HMOs produced by the sucrose strain do not contain such degradation by-products.

The genetically modified cell of the invention can have more than one recombinant gene, encoding more than one glycosyl transferase enzyme which is able to transfer the glycosyl residue of an activated sugar nucleotide to an internalized acceptor molecule or the previously glycosylated acceptor made by the same cell, so the oligosaccharide product is formed from the internalized acceptor by multiple glycosyl transfer mediated by multiple glycosyl transferases expressed by the cell. Accordingly, the resulting oligosaccharide product can be a glycosylated lactose or a glycoside thereof. The glycosylated lactose is preferably an N-acetyl-glucosaminylated, galactosylated, fucosylated and/or sialylated lactose. In order to produce these derivatives the cell comprises one or more recombinant genes encoding an N-acetyl-glucosaminyl transferase, a galactosyl transferase, a sialyl transferase and/or a fucosyl transferase, and also comprise a biosynthetic pathway to the corresponding activated sugar type nucleotides, that is UDP-GlcNAc, UDP-Gal, GDP-Fuc and/or CMP-sialic acid.

According to a preferred embodiment, the genetically modified E. coli cell is suitable for producing a neutral HMO, preferably of 3-6 monosaccharide units, and comprises (ia)—a recombinant gene encoding a N-acetyl-glucosaminyl transferase enzyme which is able to transfer the GlcNAc of UDP-GlcNAc to the internalized lactose or to an intermediate in the biosynthetic pathway to said neutral HMO from lactose, and one or more genes encoding a biosynthetic pathway to UDP-GlcNAc; and/or a recombinant gene encoding a fucosyl transferase enzyme which is able to transfer the fucosyl residue of GDP-Fuc to the internalized lactose or to an intermediate in the biosynthetic pathway to said neutral HMO from lactose, and one or more genes encoding a biosynthetic pathway to GDP-Fuc, (ib)—optionally a recombinant gene encoding a galactosyl transferase enzyme which is able to transfer the galactosyl residue of UDP-Gal to an intermediate in the biosynthetic pathway to said neutral HMO from lactose, and one or more genes encoding a biosynthetic pathway to UDP-Gal, characterized in that the cell also comprises a heterologous PTS-dependent sucrose utilization system to provide sucrose as a carbon source, as well as an energy source, for biosynthesis of UDP-GlcNAc and/or GDP-Fuc, and optionally UDP-Gal by the cell, and as energy source for making said neutral HMO. The heterologous PTS-dependent sucrose utilization system preferably comprises scr genes, more preferably scrY, scrA, scrB and scrR, and particularly does not contain scrK.

According to a preferred embodiment, the genetically modified E. coli cell suitable for producing an N-acetylated HMO, preferably of 3-6 monosaccharide units, comprises:

a recombinant gene encoding a N-acetyl-glucosaminyl transferase enzyme which is able to transfer the GlcNAc of UDP-GlcNAc to the internalized lactose or to an intermediate in the biosynthetic pathway to said N-acetylated HMO from lactose, optionally a recombinant gene encoding a galactosyl transferase enzyme which is able to transfer the galactosyl residue of UDP-Gal to the N-acetyl-glucosaminylated lactose or to an intermediate in the biosynthetic pathway to said N-acetylated HMO from lactose, and one or more genes encoding a biosynthetic pathway to UDP-GlcNAc and optionally to UDP-Gal, characterized in that the cell also comprises a heterologous PTS-dependent sucrose utilization system to provide sucrose as a carbon source, as well as an energy source, for biosynthesis of UDP-GlcNAc and optionally UDP-Gal by the cell, and as energy source for making said N-acetylated HMO. The heterologous PTS-dependent sucrose utilization system preferably comprises scr genes, more preferably scrY, scrA, scrB and scrR, and particularly does not contain scrK.

If the N-acetyl-glucosaminyl transferase is a β-1,3-N-acetyl-glucosaminyl transferase and no recombinant gene encoding a galactosyl transferase is present in the cell, the product is preferably lacto-N-triose II, and if a β-1,3- or a β-1,4-galactosyl transferase is also present in the cell, the product is preferably LNT or LNnT, respectively.

According to another preferred embodiment, the genetically modified E. coli cell is suitable for producing a fucosylated N-acetylated HMO, preferably LNFP-I, LNFP-II, LNFP-III, LNFP-V, LNFP-VI, LNDFH-I, LNDFH-II or LNDFH-III, and comprises:

a recombinant gene encoding an N-acetyl-glucosaminyl transferase enzyme which is able to transfer the GlcNAc of UDP-GlcNAc to the internalized lactose or to an intermediate in the biosynthetic pathway to said fucosylated N-acetylated HMO from lactose, and one or more genes encoding a biosynthetic pathway to UDP-GlcNAc;

a recombinant gene encoding a fucosyl transferase enzyme which is able to transfer the fucosyl residue of GDP-Fuc to the internalized lactose or to an intermediate in the biosynthetic pathway to said fucosylated N-acetylated HMO from lactose, and one or more genes encoding a biosynthetic pathway to GDP-Fuc, and a recombinant gene encoding a galactosyl transferase enzyme which is able to transfer the galactosyl residue of UDP-Gal to an intermediate in the biosynthetic pathway to said fucosylated N-acetylated HMO from lactose, and one or more genes encoding a biosynthetic pathway to UDP-Gal, characterized in that the cell also comprises a heterologous PTS-dependent sucrose utilization system to provide sucrose as a carbon source, as well as an energy source, for biosynthesis of UDP-GlcNAc, GDP-Fuc and UDP-Gal by the cell, and as energy source for making said fucosylated N-acetylated HMO. The heterologous PTS-dependent sucrose utilization system preferably comprises scr genes, more preferably scrY, scrA, scrB and scrR, and particularly does not contain scrK.

According to yet another preferred embodiment, the genetically modified *E. coli* cell is suitable for producing a fucosylated HMO, preferably 2'-FL, 3-FL or DFL, and comprises:

a recombinant gene encoding a fucosyl transferase enzyme which is able to transfer the fucosyl residue of GDP-Fuc to the internalized lactose, and one or more genes encoding a biosynthetic pathway to GDP-Fuc, characterized in that the cell also comprises a heterologous PTS-dependent sucrose utilization system to provide sucrose as a carbon source, as well as an energy source, for biosynthesis of GDP-Fuc by the cell, and as energy source for making said fucosylated HMO. The heterologous PTS-dependent sucrose utilization system preferably comprises scr genes, more preferably scrY, scrA, scrB and scrR, and particularly does not contain scrK.

If the fucosyl transferase is an α-1,2-fucosyl transferase, the product is preferably 2'-fucosyllactose, if the fucosyl transferase is an α-1,3-fucosyl transferase, the product is preferably 3-fucosyllactose, and if both α-1,2- and α-1,3-fucosyl transferases are expressed in the cell, the product is preferably difucosyllactose.

According to still another preferred embodiment, the genetically modified *E. coli* cell suitable for producing a sialylated HMO, preferably of 3-5 monosaccharide units, more preferably a sialylated lactose, comprises:

a recombinant gene encoding a sialyl transferase enzyme which is able to transfer the sialyl residue of CMP-sialic acid to the internalized lactose or to an intermediate in the biosynthetic pathway to said sialylated HMO from lactose, and one or more genes encoding a biosynthetic pathway to CMP-sialic acid, characterized in that the cell also comprises a heterologous PTS-dependent sucrose utilization system to provide sucrose as a carbon source, as well as an energy source, for biosynthesis of CMP-sialic acid by the cell, and as energy source for making said sialylated HMO. The heterologous PTS-dependent sucrose utilization system preferably comprises scr genes, more preferably scrY, scrA, scrB and scrR, and particularly does not contain scrK.

If the sialyl transferase is an α-2,3-sialyl transferase, the product is preferably 3'-sialyllactose, and if the sialyl transferase is an α-2,6-sialyl transferase, the product is preferably 6'-sialyllactose.

According to another preferred embodiment, the genetically modified *E. coli* cell suitable for producing a fucosylated and sialylated HMO, preferably of 3-5 monosaccharide units, more preferably a sialyl-fucosyl-lactose, comprises:

a recombinant gene encoding a sialyl transferase enzyme which is able to transfer the sialyl residue of CMP-sialic acid to the internalized lactose or to an intermediate in the biosynthetic pathway to said fucosylated and sialylated HMO from lactose, a recombinant gene encoding a fucosyl transferase enzyme which is able to transfer the fucosyl residue of GDP-Fuc to the internalized lactose or to an intermediate in the biosynthetic pathway to said fucosylated and sialylated HMO from lactose, and one or more genes encoding a biosynthetic pathway to CMP-sialic acid and GDP-Fuc, characterized in that the cell also comprises a heterologous PTS-dependent sucrose utilization system to provide sucrose as a carbon source, as well as an energy source, for biosynthesis of CMP-sialic acid and GDP-Fuc by the cell, and as energy source for making said fucosylated and sialylated HMO. The heterologous PTS-dependent sucrose utilization system preferably comprises scr genes, more preferably scrY, scrA, scrB and scrR, and particularly does not contain scrK.

If the sialyl transferase is an α-2,3-sialyl transferase and the fucosyl transferase is an α-1,3-fucosyl transferase, the product is preferably 3'-sialyl-3-fucosyllactose.

According to another preferred embodiment, the genetically modified *E. coli* cell is suitable for producing a fucosylated LNT or LNnT and comprises:

a recombinant gene encoding a N-acetyl-glucosaminyl transferase enzyme which is able to transfer the GlcNAc of UDP-GlcNAc to the internalized lactose to make lacto-N-triose, a recombinant gene encoding a galactosyl transferase enzyme which is able to transfer the galactosyl residue of UDP-Gal to the lacto-N-triose to make LNT or LNnT, a recombinant gene encoding a fucosyl transferase enzyme which is able to transfer the fucosyl residue of GDP-Fuc to the LNT or LNnT, one or more genes encoding a biosynthetic pathway to GDP-Fuc one or more genes encoding a biosynthetic pathway to UDP-GlcNAc and to UDP-Gal, characterized in that the cell also comprises a heterologous PTS-dependent sucrose utilization system to provide sucrose as a carbon source, as well as an energy source, for biosynthesis of UDP-GlcNAc, UDP-Gal and GDP-Fuc by the cell, and as energy source for making said fucosylated LNT or LNnT. The heterologous PTS-dependent sucrose utilization system preferably comprises scr genes, more preferably scrY, scrA, scrB and scrR, and particularly does not contain scrK.

EXAMPLES

Example 1: Comparative Test for Making LNnT by a Glycerol or Sucrose Utilizing *E. coli*

Bacterial Strains:

Both strains were constructed from *Escherichia coli* K12 strain DH1 which was obtained from the Deutsche Sammlung von Mikroorganismen (reference DSM 5346) by deleting the genes: lacZ nanKETA lacA melA wcaJ mdoH, by inserting a Plac promoter, and maintaining genes involved in the UDP-GlcNAc and UDP-Gal biosynthesis. The glycerol utilizing strain (strain I) contains a pBBR3- lgtA-tet plasmid carrying *N. meningitidis* lgtA gene for β-1,3-N-acetylglucosaminyl transferase and the tetracycline resistant gene, and a pBS-galT-amp plasmid carrying *Helicobacter pylori* galT gene for β-1-4-galactosyl transferase and the ampicillin resistant gene. The sucrose utilizing strain (strain II) contains the two following plasmids:

- pBS-scrBR-galT-amp which is a pUC derivative carrying the galT gene encoding an β-1,4-galactosyl transferase, the scrR gene encoding a sucrose repressor, the scrB gene encoding a sucrose-6-phosphate hydrolase and the ampicillin resistance gene;
- pBBR3-scrYA-lgtA-tet which is a pBBR1-MCS3 derivative carrying the lgtA gene encoding a β-1,3-N-acetylglucosaminyl transferase, the scrA gene encoding a PTS system sucrose-specific EIIBC component, the scrY gene encoding a sucrose porin and the tetracycline resistance gene.

Fermentation Procedure:

Glucose, glycerol, sucrose and lactose were each sterilized at 120° C. Isopropyl thio-β-D-galactopyranoside (IPTG) was filter sterilized.

The culture was carried out in a 3 l fermenter containing ≈0.9 l of mineral culture medium (Samain et al. *J. Biotechnol.* 72, 33 (1999); does not contain antibiotics for the sucrose system). The temperature was kept at 33° C. and the pH regulated at 6.8 with 28% $NH_4OH$. The inoculum of the producing strain consisted in a LB medium (20 ml) supplemented with ampicillin and tetracycline for strain I or M9 medium (20 ml) supplemented with sucrose for strain II was added to the fermenter. The exponential growth phase started with the inoculation and stopped until exhaustion of the carbon source (glucose for strain I or sucrose for strain II, ≈17.5 g/l) initially added to the medium. A lactose solution (70 g of lactose/500 ml of water) was then added before starting the feeding with the carbon source (500 g/l solution, 4.5 g/h of glycerol for strain I and 3 g/h of sucrose for strain II). The inducer (isopropyl thio-β-D-galactopyranoside, IPTG, 1-2 ml of a 50 mg/ml solution) was also added. The glycerol-fed fermentation (strain I) lasted for 90 hours after which the cells died (LNnT titre: 45 g/l). The sucrose-fed fermentation (strain II) produced an LNnT concentration of 56 g/l after 116 hours.

Example 2: Production of 2'-FL by a Sucrose Utilizing *E. coli*

Bacterial Strain:

The strain was constructed from *Escherichia coli* K12 strain DH1 which was obtained from the Deutsche Sammlung von Mikroorganismen (reference DSM 5346) by deleting the genes: lacZ nanKETA lacA melA wcaJ mdoH and by inserting a Plac promoter to upstream the gmd gene. In addition the strain contains the following plasmids:

- pBS-futC-scrBR-amp which is a pUC derivative carrying the futC gene encoding an α-1,2-fucosyl transferase, the scrR gene encoding a sucrose repressor, the scrB gene encoding a sucrose-6-phosphate hydrolase and the ampicillin resistance gene;
- pBBR3-GMAB-scrYA-tet which is a pBBR1-MCS3 derivative carrying the manB, manC, gmd and wcaG genes involved in the GDP-Fuc biosynthesis, the scrA gene encoding a PTS system sucrose-specific EIIBC component, the scrY gene encoding a sucrose porin and the tetracycline resistance gene.

Fermentation Procedure:

Sucrose and lactose were each sterilized at 120° C. Isopropyl thio-β-D-galactopyranoside (IPTG) was filter sterilized.

The culture was carried out in a 2 l fermenter containing ≈0.9 l of mineral culture medium (Samain et al. *J. Biotechnol.* 72, 33 (1999); does not contain antibiotics). The temperature was kept at 33° C. and the pH regulated at 6.8 with 28% $NH_4OH$. The inoculum of the producing strain consisted in a M9 medium supplemented with sucrose (20 ml) was added to the fermenter. The exponential growth phase started with the inoculation and stopped until exhaustion of sucrose (≈22 g/l) initially added to the medium. The inducer (isopropyl thio-β-D-galactopyranoside, IPTG, 1-2 ml of a 50 mg/ml solution) was then added. A feeding with a lactose+sucrose solution (160 g of lactose+500 g of sucrose/l in water) started with a rate of 9 ml/h for 6 hours, then was continued for 115 hours at a rate of 6 ml/h. The concentration of 2'-FL was around 100 g/l in the supernatant at the end of the fermentation.

Example 3: Comparative Test for Making 2'-FL by a Glucose or Sucrose Utilizing *E. coli*

Gene targeting in the chromosomal DNA was done using standard DNA manipulation techniques, e.g. as disclosed in Warming et al. *Nucleic Acids Res.* 33, e36 (2005). Insertion of genetic cassettes in the chromosomal DNA was done by gene Gorging as described by Herring et al. *Gene* 311, 153 (2003).

The strains were derived from an *E. coli* platform strain that was constructed from *E. coli* K12 DH1 (genotype: $F^-$, $\lambda^-$, gyrA96, recA1, relA1, endA1, thi-1, hsdR17, supE44, obtained from Deutsche Sammlung von Mikroorganismen and Zellkulturen (DSMZ), www.dsmz.de, reference DSM 4235) by disrupting (deletions of) the genes lacZ, nanKETA, lacA, melA, wcaJ, mdoH and by inserting a Plac promoter upstream the gmd gene. In addition, two copies of codon optimized futC encoding an α1,2-fucosyl transferase under the control of the glpF promoter were integrated into the genome (chromosome) of the *E. coli* platform strain in loci related to sugar metabolism and expressed under the control of the glpF promoter (see WO 2019/123324); a single copy of the colanic acid cluster (gmd-wcaG-wcaH-wcaI-manC-manB) was integrated in a locus involved in the utilization of alternative carbon sources and expressed under the control of the glpF promoter; lacI was deleted from the lac operon (ΔlacI); hlyE gene, coding for the toxin cytolysin A, was deleted (in order to obtain a safer manufacturing strain, eliminating the risk of unintended expression of the toxin); and the functional regulatory gene glpR, which is a repressor of the glpF promoter, were deleted (see WO 2019/123324). The resulting strain was able to produce 2'-FL when grown on glucose, however, was not able to grow on sucrose (strain 1). To make it able to grow on sucrose, strain 1 was further modified by inserting a) scrYA from *Klebsiella pneumoniae* (GeneBank accession ID: X57401.1) in another locus involved in sugar metabolism and expressed under the control of a glpF promoter with a modified SD sequence (PglpF_SD1, see WO 2019/123324), b) scrBR from *Salmonella thyphimurium* (GeneBank accession ID: NG_034574.1) in one of the loci that enables sugar metabolism under the control of the Pscr promoter (strain 2). The strains are plasmid-free.

The fermentations were carried out in 250 ml fermenters (DASBOX Mini Bioreactor system, Eppendorf) starting with 100 ml of defined mineral culture medium, consisting of 25 g/kg carbon source (glucose or sucrose), $(NH_4)_2HPO_4$, $KH_2PO_4$, $MgSO_4 \times 7H_2O$, KOH, NaOH, trace element solution, citric acid, antifoam and thiamine. The trace element solution contained Mn, Cu, Fe, Zn as sulfate salts and citric acid. Lactose was added pre-inoculation at 80 g/kg. The pH throughout fermentation was controlled at 6.8 by titration with 14% $NH_4OH$ solution. Aeration was at 1 vvm using air and dissolved oxygen was controlled above 20% of air saturation. Fermentations were started by inoculation with 2% (v/v) of pre-cultures grown in a similar medium. After depletion of the carbon source contained in the batch medium, a sterile feed solution containing glucose or sucrose, $MgSO_4 \times 7H_2O$, trace metal solution and lactose was fed continuously at a constant feed rate in a carbon-limited manner. The lactose concentration in the broth was maintained above 15 g/kg throughout and until the end of the fermentations. End-of-fermentation was at approximately 120 hours.

Throughout the fermentation, samples were taken in order to determine the concentration of 2'-FL, DFL, lactose and other minor by-products using HPLC. Total broth samples were diluted three-fold in deionized water and boiled for 20 minutes. This was followed by centrifugation at 17000 g for 3 minutes, where after the resulting supernatant was analysed by HPLC. The above measurements were used to accurately calculate the 2'-FL titre, the ratio of DFL/2'-FL and the yield of 2'-FL on the carbon source.

While the only change between the two tested strains was the introduction of the sucrose operon genes on the chromosome, the fermentation data in the table below show clear evidence that by-product formation was significantly reduced by approximately 25% at the end-of-fermentation, while 2'-FL titre and yield can be at least retained or even slightly increased, compared to the glucose reference strain. The use of the sucrose technology is therefore beneficial as it facilitates the purification process. The reduced DFL formation will furthermore provide a bigger upstream process optimisation potential, since the sucrose strain does not waste as much energy on the production of the GDP-fucose precursor.

| strain | carbon source | number of replicate runs | DFL/2'-FL ratio EoF* | 2'-FL titre EoF* | 2'-FL accumulated yield index EoF* |
|---|---|---|---|---|---|
| strain 1 | glucose | 3 | 9.9% (0.6% SD**) | 124.4 g/l (1.1 g/l SD**) | 100% (6.9% SD**) |
| strain 2 | sucrose | 2 | 7.3% | 125.9 g/l | 111.5% |

*EoF = end-of-fermentation 119.3 h (±1.4 h)
**SD = standard deviation

Example 4: Comparative Test for Making 2'-FL by a Glucose or Sucrose Utilizing *E. coli*

This test comprised strain 1, disclosed in Example 3 above, and a modified strain 2, referred to as strain 2', which differs from strain 2 disclosed in Example 3 above in that the regulatory gene glpR was not deleted and thus remained functional.

The strains were fermented separately, under equivalent industrialized conditions based on the conditions disclosed in Example 3, with glucose for strain 1 and sucrose for strain 2'. The product 2'-FL was purified and isolated from the broths using identical unit step operations, without crystallization.

Analysis of the purified samples showed substantial difference in the presence of specific carbohydrate impurities. Product of strain 1 (fermented with glucose) had more than 2 w/w % of glucose degradation products, containing (amongst other products) isomaltose, kojibiose, gentiobiose and nigerose, while the product of strain 2' (fermented with sucrose) was totally free of these impurities. Furthermore, the sucrose-manufactured product is extremely low in the sum of unspecified impurities compared to the glucose-manufactured product, i.e. 0.05 w/w % vs 0.26 w/w %. The overall advantage of the sucrose technology is thereby two-fold, firstly to obtain a product with higher purity (thereby alleviating the need for costly crystallisation) and secondly, a 2% higher carbon efficiency, since the carbon source upon heat sterilisation was not converted into non-metabolisable carbohydrate impurities.

Example 5: Comparative Test for Making LNT

A strain was derived from an *E. coli* platform strain that was constructed from *E. coli* K12 DH1 (genotype: F⁻, λ⁻, gyrA96, recA1, relA1, endA1, thi-1, hsdR17, supE44, obtained from Deutsche Sammlung von Mikroorganismen and Zellkulturen (DSMZ), www.dsmz.de, reference DSM 4235) by disrupting (deletions of) the genes lacZ, nanKETA, lacA, melA, wcaJ, mdoH and by inserting a Plac promoter upstream the gmd gene. In addition, three copies of codon optimized IgtA coding sequence for β1,3-N-acetyl glucosaminyl transferase were integrated into the genome (chromosome) of the *E. coli* platform strain in loci related to sugar metabolism and expressed under the control of the glpF promoter; two copies of codon optimized galTK encoding β1,3-galactosyl transferase (WO 2020/115671) was integrated into the genome of the *E. coli* platform strain in another loci involved in sugar metabolism and expressed under the control of the glpF promoter. The integration of the genes of the sucrose operon scrYABR (while split into scrYA and scrBR) was done at two sites in the mixed-acid fermentation pathway, thereby deleting genes that cause formation of undesired fermentative metabolites under anaerobic conditions, but not under normal aerobic fermentation conditions. In addition, an expression cassette containing the glpF promoter linked to a codon optimized DNA encoding a putative MFS transporter protein from *Rosenbergiella nectarea* (GenBank accession ID: WP_092672081.1), which facilitates the export of LNT from the cell, was inserted in a locus involved in the utilization of alternative carbon sources. Moreover, lacI and hlyE were deleted. The so-constructed strain is plasmid-free and able to grow on glucose and sucrose.

The fermentations were carried out in 250 ml fermenters (DASBOX Mini Bioreactor system, Eppendorf) starting with 100 ml of defined mineral culture medium, consisting of 30 g/kg carbon source (glucose or sucrose), $(NH_4)_2HPO_4$, $KH_2PO_4$, $MgSO_4 \times 7H_2O$, KOH, NaOH, trace element solution, citric acid, antifoam and thiamine. The trace element solution contained Mn, Cu, Fe, Zn as sulfate salts and citric acid. Lactose was provided by bolus addition of 80 g/kg approximately 5 hours after the end of the batch phase, i.e. at approximately 18-19 h elapsed fermentation time (ELT). The pH throughout fermentation was controlled at 6.8 by titration with 14% $NH_4OH$-solution. Aeration was at 1 vvm using air and dissolved oxygen was controlled above 23% of air saturation. Fermentations were started by inoculation with 2% (v/v) of pre-cultures grown in a similar medium. After depletion of the carbon source contained in the batch medium, a sterile feed solution containing glucose or sucrose, (NH$_4$)$_2$SO$_4$, trace metal solution and anti-foam was fed continuously at a constant feed rate in a carbon-limited manner. Lactose was almost depleted at 72.8 h ELT in the sucrose fermentations, while it was still at around 8-10 g/l in the glucose fermentation, indicating a higher lactose utilisation rate and hence product formation. End-of-fermentation samples were taken and analysed at 72.8 h.

Throughout the fermentation, samples were taken in order to determine the concentration of LNT and lactose. Total broth samples were diluted three-fold in deionized water and boiled for 20 minutes. This was followed by centrifugation at 17000 g for 3 minutes, where after the resulting supernatant was analysed by HPLC. The HPLC measurements were used to accurately calculate the LNT titre, by-product ratios (not shown) and the accumulated yield of LNT on the carbon source. The latter takes also smaller variations in feed rates and dilutions into account and is therefore an important parameter for direct comparison.

This study describes a direct comparison of a sucrose-utilising strain in fermentations with sucrose versus glucose as carbon source. The processes were identical except for the type of carbon source used. The data demonstrate clearly superiority of sucrose in terms of LNT productivity and carbon yield. The table below shows that the average carbon yield was increased by 17% when using sucrose instead of glucose. This is also reflected by the 19% higher final LNT titre at end-of-fermentation and the increased lactose consumption rate (lactose was only added by bolus addition and not in the feed solution). Overall, the use of the sucrose technology is therefore beneficial as it not only facilitates the purification process due to the higher final titre, but also leads to a more efficient carbon source conversion to product.

| carbon source | number of replicate runs | lactose concentration EoF* | LNT titre EoF* | LNT accumulated yield index EoF* |
|---|---|---|---|---|
| sucrose | 2 | 1.6 g/l | 78.1 g/l | 117.5% |
| glucose | 2 | 9.2 g/l | 65.4 g/l | 100% |

*EoF = end-of-fermentation 72.8 h

The invention claimed is:
1. A genetically modified microorganism for making an oligosaccharide or a glycoside of said oligosaccharide, comprising:
   a recombinant gene encoding a glycosyl transferase which can transfer a glycosyl residue of an activated sugar nucleotide to a carbohydrate acceptor or a glycoside of said acceptor,
   a biosynthetic pathway for making said activated sugar nucleotide from sucrose, and
   one or more genes encoding a heterologous PTS-dependent sucrose utilization system, so that said cell is capable to use sucrose as a carbon source for making said activated sugar nucleotide and as energy source for making said oligosaccharide,
wherein the carbohydrate acceptor is not sucrose,
wherein said genetically modified microorganism is an *E. coli* cell of LacZ-genotype,
said recombinant oligosaccharide is 2'-fucosyllactose (2'-FL),
said activated sugar nucleotide is GDP-Fuc,
said glycosyl transferase is an α-1,2-fucosyltransferase,
and said heterologous PTS-dependent sucrose utilization system comprises proteins encoded by scr genes scrY for a sucrose porin, scrA for a PTS permease, scrB for a sucrose-6-phosphate hydrolase and scrR for a repressor protein.
2. The genetically modified microorganism of claim 1, wherein the glycosyl transferase can transfer a glycosyl residue to a carbohydrate acceptor internalized by the microorganism.
3. The genetically modified microorganism of claim 2, wherein the glycosyl transferase can transfer a glycosyl residue of an activated sugar nucleotide to an intermediate in the biosynthetic pathway to said oligosaccharide from said acceptor.
4. The genetically modified microorganism of claim 1, wherein an aglycon in the glycoside of a recombinant oligosaccharide or a carbohydrate acceptor is selected from the group consisting of:
   —OR$_A$, wherein R$_A$ is a linear or branched hydrocarbon chain having, when saturated, 1-24 carbon atoms or, when unsaturated, 2-24, carbon atoms, or R$_A$ means an aryl moiety, or R$_A$ means a group removable by hydrogenolysis,
   —X—R$_B$, wherein X is N or S, and R$_B$ means linear or branched hydrocarbon chain having, when saturated, 1-24 carbon atoms or, when unsaturated, 2-24 carbon atoms, or R$_B$ means an aryl moiety, or R$_B$ means a benzyl group,
   a group that links an anomeric carbon atom and an adjacent carbon atom to each other by a —NH—C(=O)—O— bridge, thus forming a fused 5-membered ring, as depicted in case of an aldose:

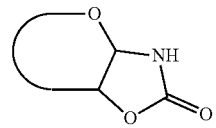

azide,
—NH—C(R")=C(R')2, wherein each R' independently is an electron withdrawing group selected from —CN, —COOH, —COO-alkyl, —CO-alkyl, —CONH2, —CONH-alkyl and —CON(alkyl)$_2$, or wherein the two R'-groups are linked together and form —CO—(CH$_2$)$_{2-4}$—CO— and thus form with the carbon atom, to which they are attached, a 5-7 membered cycloalkane-1,3-dione, in which dione any of its methylene groups is optionally substituted with 1 or 2 alkyl groups, and wherein R" is H or alkyl,
a residue of an amino acid,
a polyethylene glycol residue,
a polyvinyl alcohol residue, and
an α,β-unsaturated amido group of formula A or an α,β-unsaturated carbonyl group of formula B

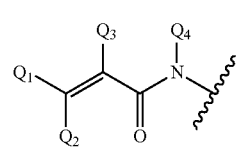

A

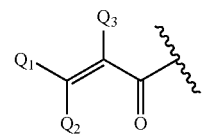

B wherein Q2, Q3 and Q4 are, independently, H and $C_1$-$C_6$-alkyl, which alkyl is optionally substituted with halogen, OH, nitro or phenyl groups.

5. The genetically modified microorganism of claim 1, wherein one or more of the following genes are deleted or deactivated: lacI, lacA, and hlyE.

6. The genetically modified microorganism of claim 1, wherein recombinant gene encoding a glycosyl transferase is chromosomally integrated in the microorganism.

7. The genetically modified microorganism of claim 1, wherein the scr genes are chromosomally integrated in the genome of the microorganism.

8. The genetically modified microorganism of claim 1 which is plasmid-free.

9. The genetically modified microorganism of claim 1, wherein the *E. coli* comprises:
   a recombinant gene encoding a fucosyl transferase enzyme which is able to transfer a fucosyl residue of GDP-Fuc to an internalized lactose, and
   one or more genes encoding a biosynthetic pathway to GDP-Fuc.

10. A process for making an oligosaccharide or a glycoside of said oligosaccharide by glycosylating a carbohydrate acceptor, or a glycoside of said acceptor, wherein the carbohydrate acceptor is not sucrose, comprising the steps of:
    a) providing of a genetically modified microorganism of claim 1,
    b) culturing said cell in the presence of said acceptor and sucrose, and
    c) separating said oligosaccharide from said cell, from the culture medium or from both.

11. The genetically modified microorganism of claim 1, wherein the genetically modified microorganism further comprises a deleted lacA gene.

12. The genetically modified microorganism of claim 1, wherein the genetically modified microorganism further comprises a deleted lacI gene.

13. The genetically modified microorganism of claim 1, wherein the genetically modified microorganism further comprises a deleted hlyE gene.

* * * * *